United States Patent
Buhac

(10) Patent No.: US 10,330,570 B1
(45) Date of Patent: *Jun. 25, 2019

(54) COMPACTION TESTING SAMPLER ASSEMBLY

(71) Applicant: H. Joseph Buhac, Columbus, OH (US)

(72) Inventor: H. Joseph Buhac, Columbus, OH (US)

( * ) Notice: Subject to any disclaimer, the term of this patent is extended or adjusted under 35 U.S.C. 154(b) by 258 days.

This patent is subject to a terminal disclaimer.

(21) Appl. No.: 15/611,872

(22) Filed: Jun. 2, 2017

Related U.S. Application Data

(63) Continuation-in-part of application No. 14/693,107, filed on Apr. 22, 2015, now Pat. No. 9,671,385.

(60) Provisional application No. 61/993,567, filed on May 15, 2014.

(51) Int. Cl.
| | |
|---|---|
| *G01N 1/04* | (2006.01) |
| *G01N 1/28* | (2006.01) |
| *G01N 33/38* | (2006.01) |

(52) U.S. Cl.
CPC .............. *G01N 1/04* (2013.01); *G01N 1/286* (2013.01); *G01N 33/383* (2013.01)

(58) Field of Classification Search
CPC ....................................................... G01N 1/04
See application file for complete search history.

(56) References Cited

U.S. PATENT DOCUMENTS

| | | | | |
|---|---|---|---|---|
| 3,685,302 A | * | 8/1972 | Fuller | E02D 5/44 405/237 |
| 5,069,417 A | * | 12/1991 | Boss | B28B 7/0094 249/136 |
| 6,354,766 B1 | * | 3/2002 | Fox | E02D 3/08 405/232 |
| 9,671,385 B2 | * | 6/2017 | Buhac | G01N 33/383 |

* cited by examiner

*Primary Examiner* — Noam Reisner
*Assistant Examiner* — Dennis Hancock
(74) *Attorney, Agent, or Firm* — Ralph E. Jocke; Walker & Jocke

(57) ABSTRACT

An in-situ roller compacted concrete testing sampler assembly is provided. The testing sampler assembly includes a first tube and a second tube. The second tube is configured to contain a roller compacted sample. The first tube and the second tube are configured to be placed in a loose roller compacted concrete lift for a construction site, and compacted simultaneously during the compaction of the loose roller compacted concrete lift. The second tube is configure to move with respect to the first tube to compact the roller compacted sample during compaction of the loose roller compacted concrete lift.

20 Claims, 15 Drawing Sheets

COMPACTION TESTING SAMPLER ASSEMBLY

BACKGROUND

An exemplary embodiment of this invention is directed to an apparatus and method for testing of Roller Compacted Concrete (RCC), specifically in-situ, real-time monitoring of the RCC's moisture, densities and strength.

The RCC mix includes a damp fill, a mixture of low water content, cement, fly ash and aggregate. The RCC mix is transported to the construction site by trucks or by conveyers quickly after it is mixed. The RCC mix is then dumped and spread in large quantities in 14-inch thick loose lifts using earth moving equipment. Immediately following the placement in the loose lifts, the loose lifts are compacted with a vibratory roller to the densities required by the specifications.

Referring to FIG. 1, when a loose RCC lift 20 is placed over a firm base 22 of a previously compacted RCC lift, and compacted by a vibratory roller 24, it will compress, as shown in FIG. 1. This compression is achieved under confined lift conditions, in which a change of lift volume is due to vertical movement only, i.e. vertical adjustment of granular aggregate particles as a result of combined effort of the vibratory roller's static pressure and dynamic impact.

When a compaction sampler is embedded into a loose RCC lift 20 and compacted it will sink together with the loose RCC lift 20 at the rate equal to the vertical adjustment of lift's granular particles, under the same applied compaction loads.

The lateral shifting of the RCC lift 20, under the applied compaction load and the lift confined conditions is minimal. Compression of the loose RCC lift 20 will occur between a firm base 22 of the RCC lift 20 and the surface 26 of the loose RCC lift 20 at which the compaction load is applied. Compression will be the greatest at the surface of the loose lift at t(s), and it will be reduced with an increase in a depth of the lift 20 below its initial loose surface 26. The compression value will be a smaller at the middle of compacting RCC lift at t(m), and it will reach a minimum value t(b) at the bottom of the lift 20, i.e. at the top of the firm base 22. The compressibility of the loose RCC lift 20, under the same applied compaction load may still vary between the different measuring points. This variation will depend on the variation of the initial density and moisture content of loose RCC lift material at two different locations. However, compressibility along any vertical plane within the loose RCC lift 20 at, and in an immediate vicinity of each measuring point will be the same.

The most important step in the monitoring process of a rapidly placed RCC lift, at various locations is the direct testing of the RCC lift moisture, density and strength, during the actual placing time and under the identical field compaction conditions. At the present time, only the indirect testing methods are being used to determine these compaction parameters, always under the indirect testing conditions that are being approximated to be as the in-situ actual testing conditions of the compacting RCC lifts. The current indirect testing methods provide delayed and inconsistent test results as discussed in the next section. The current indirect testing methods are used for monitoring of the in-situ moisture, densities and strength for the compacted RCC lifts. The indirect testing method for moisture and density measurements may include a nuclear gauge device and laboratory testing of RCC cylinders that are prepared individually during construction, in order to obtain various strengths of compacted RCC material. In order to obtain reliable results with a nuclear gauge, the nuclear gauge must be correctly calibrated to account for variation in composition of the mineral aggregate and its maximum size. Highly siliceous or calcareous aggregate usually produce erroneous readings, if the gauge is not properly calibrated to take into account these variations.

On the other hand, for the material that contains carbons, as bottom ash, calibration of the gauge may not be possible. Nuclear gauge measures the hydrogen in the form of water present in the compacted material. When the compacted material, such as bottom ash, contains naturally occurring hydrogen or bound hydrogen the nuclear gauge will indicate the moisture content falsely high in many cases. Some of the compacted materials showing the higher readings are: fly ash, bottom ash, cement, lime and gypsum. In addition, driving probes into compacted RCC lift that contains larger size aggregate causes some shifting-loosening of aggregate within the compacted RCC lift. This results in reduced density readings particularly in the lower section of the RCC lifts.

Regarding the laboratory testing of the RCC cylinders, the RCC cylinders are prepared in the field at the time of RCC placement. Then, the RCC mix to be compacted in the field under the actual placement conditions during construction is placed in the metal test cylinder and compacted with a metal plunger having a slightly smaller diameter than the test cylinder. The plunger is acted on by an operator or a frame mounted hammer. The test cylinders are rigid with an unyielding side wall. Thus, the compaction of the RCC material in the rigid cylinder with unyielding side wall is dependent entirely on the static compaction effort of the plunger. The vertical adjustment of the aggregate particles is different than the vertical adjustment of the RCC lift that occurs during the actual construction, since the combined compaction effort of the vibratory roller drum's static pressures and dynamic impact for the compaction of RCC material in the test cylinder is more than the compaction effort for the continuous loose RCC lift in the field due to the unyielding side wall.

Further, due to rapid placement of the RCC lifts, testing of the cylinders does not provide concurrent correlation of lift's water contents with lift's densities, i.e. the RCC strength generated within the RCC lift during actual field compaction, with the strength of the RCC mix obtained from the test cylinders which were prepared at the time of placement, but commonly tested after a subsequent RCC lift is placed. In addition, field preparation of RCC cylinders utilizes the compaction effort of either hand held or frame-mounted hammer. Neither of these compaction options generates a specified and consistent amount of compaction energy that is equivalent to the compaction effort generated by full scale compaction equipment during actual compaction of the loose RCC lift in the field.

In the case of the compaction option of using the hand held hammer, the compaction energy is operator dependent.

Therefore, a compaction energy applied to the test cylinders is inconsistent with the compaction energy applied to the RCC lift, in the field, by full scale equipment.

A sand cone method has been used also to obtain density and moisture of a low strength small aggregate RCC material, such as the bottom ash cements mixture.

However, in this method, the RCC mix that contains larger size aggregates is hard to dig after compaction, and there is always a possibility that the volume of the removed material from the hole is not totally accounted for leading to some error in the measurements. In order to minimize this error, correction for the large aggregate must be made.

Hence, it is difficult to equate the densities obtained either by the nuclear gauge, the test cylinders and sand cone with the densities achieved in the RCC lift during an actual field compaction with the full scale compaction equipment.

Methods and Apparatus for testing RCC may benefit from improvements in view of these difficulties.

SUMMARY

The following is a brief summary of subject matter that is described in greater detail herein. This summary is not intended to be limiting as to the scope of the claims.

In one exemplary embodiment, an in-situ roller compacted concrete testing sampler assembly is provided. The testing sampler assembly includes a first tube and a second tube. The second tube is configured to contain a roller compacted sample. The first tube and the second tube are configured to be placed in a loose roller compacted concrete lift for a construction site, and compacted simultaneously during the compaction of the loose roller compacted concrete lift. The second tube is configured to move with respect to the first tube to compact the roller compacted sample during compaction of the loose roller compacted concrete lift.

In another aspect of an exemplary embodiment, a method is provided for testing a roller compacted concrete sample. The method includes a) embedding a roller compacted concrete testing sampler assembly into loose roller compacted concrete lift at a construction site, wherein the testing sampler assembly comprises a first tube and a second tube, wherein the second tube is configured to contain a roller compacted sample; b) compacting the loose roller compacted concrete lift such that the second tube moves with respect to the first tube to compact the roller compacted sample during compaction of the loose roller compacted concrete lift; c) attaching a handle to the first and second tubes; and d) lifting the testing sampler out of the roller compacted concrete lift for testing.

Other aspects will be appreciated upon reading and understanding the attached figures and description.

DETAILED DESCRIPTION

Figure 1:
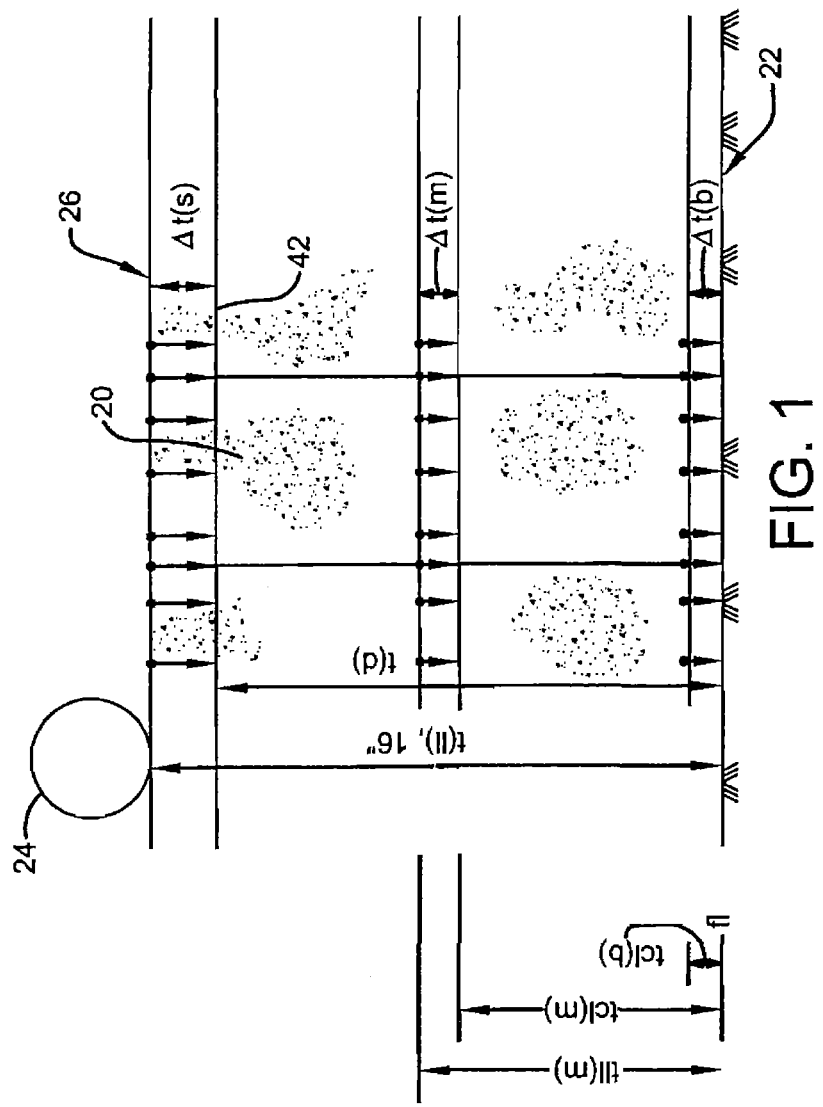
FIG. 1 shows a schematic in-situ compression of loose RCC lift, along two vertical and three horizontal planes.
Figure 2:
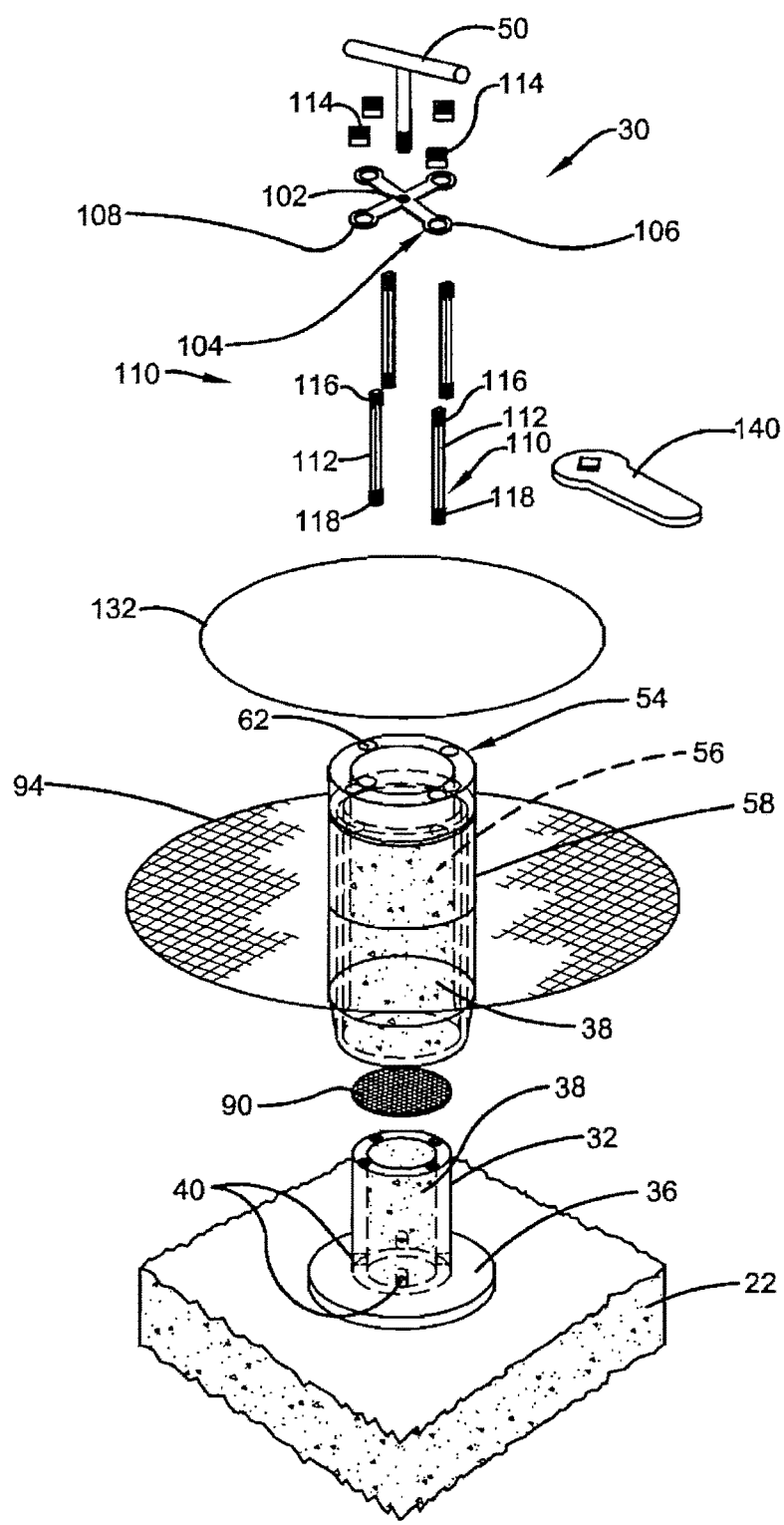
FIG. 2 shows an exploded view of an exemplary embodiment of a compaction testing sampler assembly and related elements.
Figure 3:
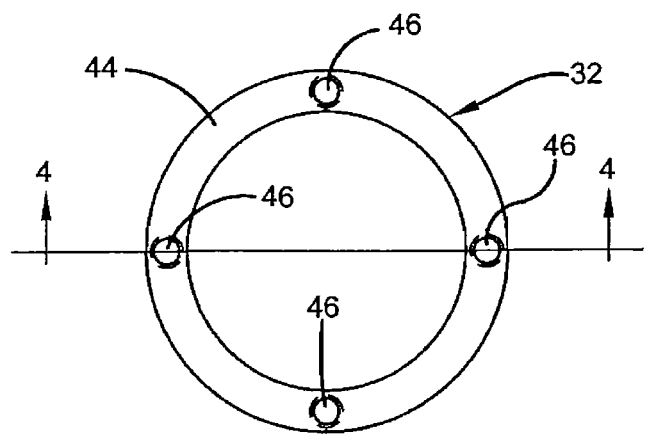
FIG. 3 shows a top plan view of the stationary tube on the firm base of the exemplary embodiment of the compaction testing sampler assembly of FIG. 2.
Figure 4:
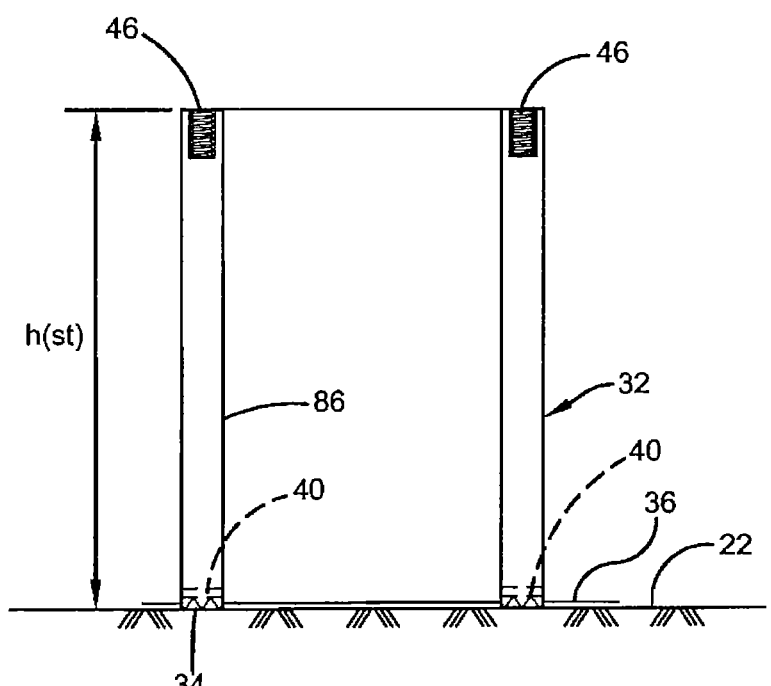
FIG. 4 shows a sectional view taken along line 4-4 of FIG. 3.
Figure 5:
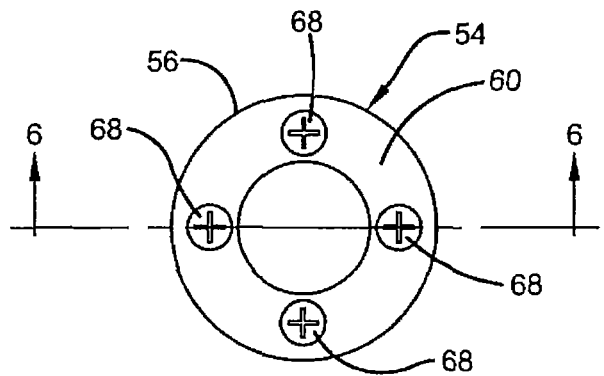
FIG. 5 shows a top plan view of the compaction testing sampler assembly.

An exemplary embodiment of an in-situ RCC compaction testing sampler assembly 30 is illustrated in FIGS. 2 through 6. Referring to FIG. 2, the testing sampler assembly 30 comprises a stationary cylindrical tube 32 and a pushing tube assembly 54. The stationary tube 32 (FIG. 4) is made in one piece of steel or other suitable material that provides years of durability. The stationary tube 32 rests upon a plastic separation membrane 36, which is laid down on the firm base 22 of a previously compacted RCC lift 20 (FIG. 1). The separation membrane 36 serves as a divider between a newly placed RCC core sample 38 and previously compacted RCC lift 20, for easier separation and retrieval of the RCC samples after compaction. The separation membrane 36 may also be made of other suitable nonbonding material than plastic. As seen in FIGS. 2 and 4, four horizontal drainage holes 40 are formed in stationary tube 32 just above the bottom of the stationary tube 32. The drainage holes 40 are equally spaced around the perimeter of the stationary tube 32. These drainage holes 40 facilitate dissipation of the pore-water pressure build-up at the bottom of stationary tube 32. As seen in FIG. 4, the stationary tube 32 includes teeth 34 that are integrally formed in a saw tooth manner around the bottom end of the stationary tube 32 and extend downwardly from the bottom end. The purpose of the castled integral teeth 34 is to provide extra "bite" into the firm base 22 to prevent lateral slipping of the stationary tube 32 on the plastic separation membrane 36 during the compaction process. Alternatively, the bottom end may not include the teeth. The stationary tube 32 may be set firmly into the surface of the compacted RCC lift 42 (FIG. 1) by tapping a hammer or other tool on a top 44 of the stationary tube 32, which should be protected as necessary, to prevent any damage during the tapping.

Figure 7:
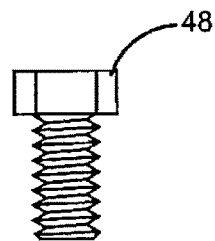
FIG. 7 shows a side plan view of a connecting bolt for another alternative lifting handle (FIG. 10) of the compaction sampler assembly of FIG. 2.

Referring to FIGS. 3 and 4, four threaded bores 46 are formed at the top 44 of the stationary tube 32 and are equally spaced around the perimeter of the top 44. Each of the bores 46 extends vertically down into the stationary tube 32. The bores 46 are sized to threadingly receive a single lifting handle 50 (FIG. 9) and single square rod (FIG. 2) or connecting bolts 48 (FIG. 7) for attachment of a double lifting handle 52 (FIG. 10) or other suitable lifting handle.

Figure 6:
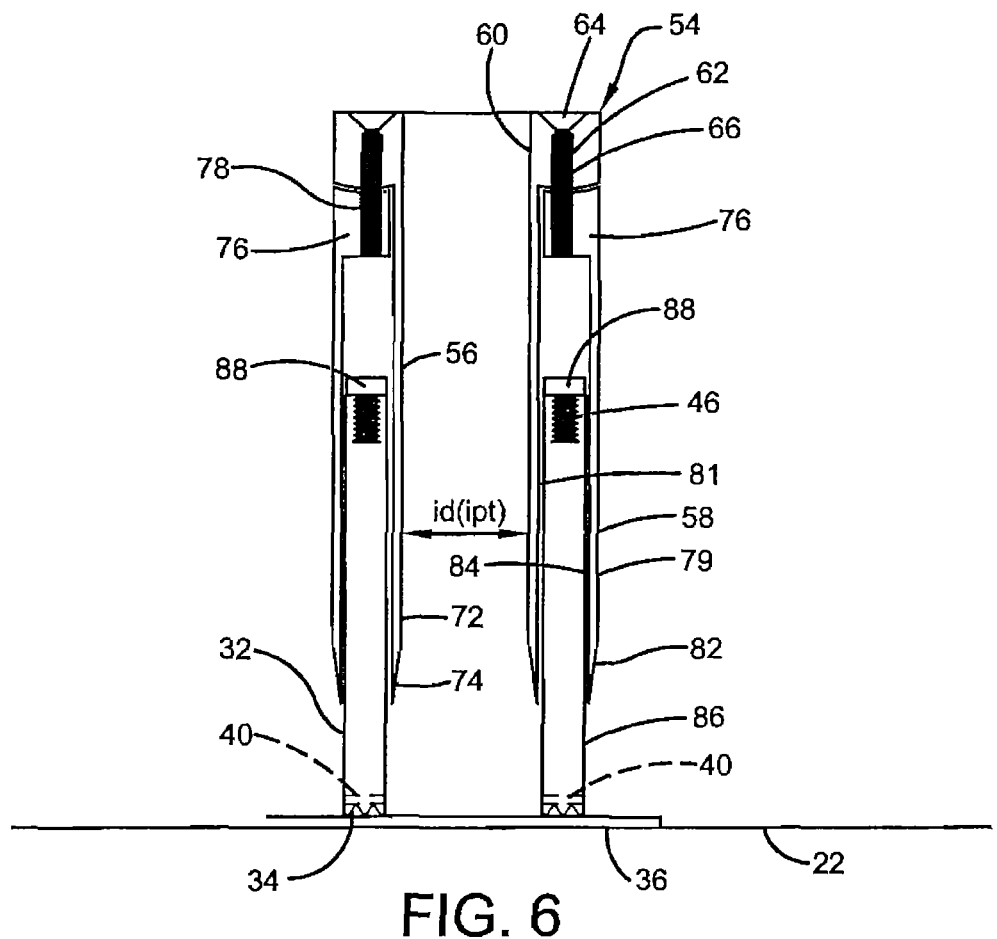
FIG. 6 shows a sectional view taken along line 6-6 of FIG. 5.
Figure 8:
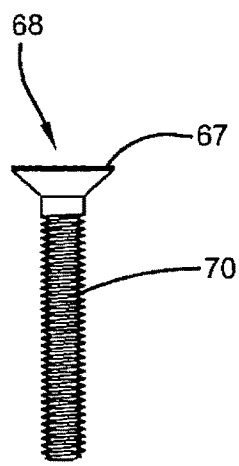
FIG. 8 shows a side plan view of a connecting bolt for connecting the inner and outer pushing tubes together of compaction testing sampler assembly of FIG. 2.
Figure 12:
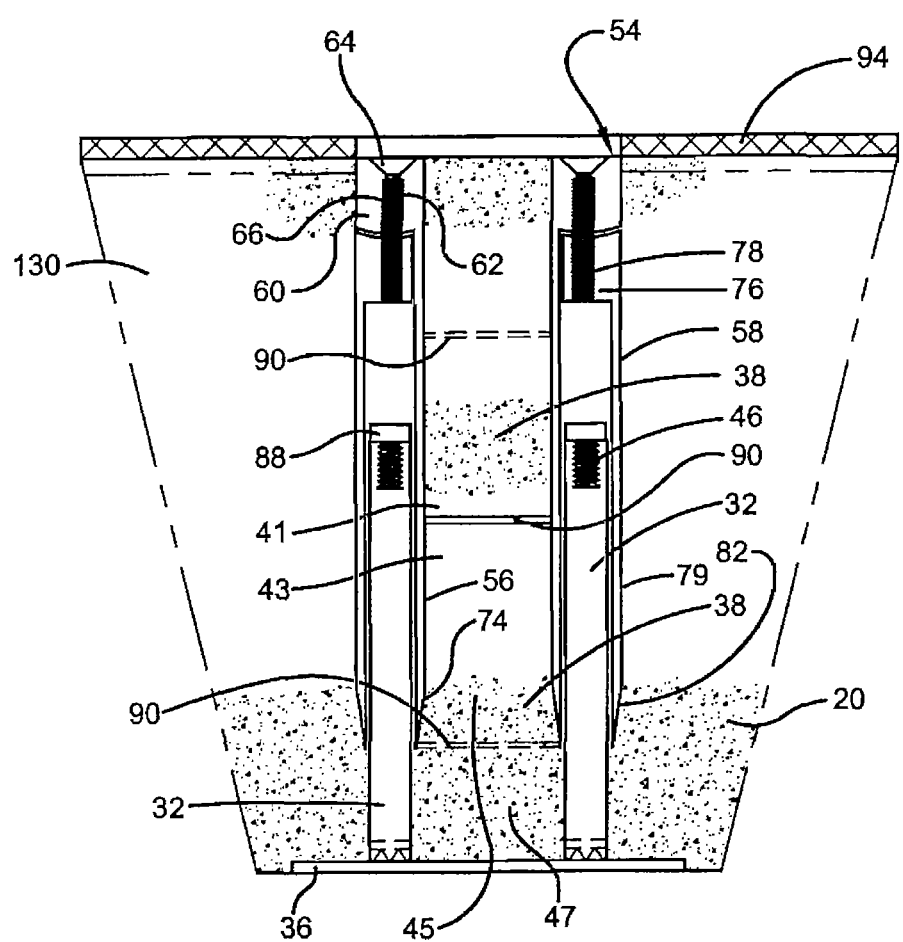
FIG. 12 shows a side sectional view of the testing sampler assembly which does not contain an old RCC core sample at the bottom of the stationary tube.

As best seen in FIGS. 2, 5, 6, and 12-15, the cylindrical pushing tube assembly 54 includes an inner pushing tube 56 and an outer pushing tube 58. The inner pushing tube 56 includes a first flange 60 integrally formed in one piece with the top of the inner pushing tube 56. The first flange 60 of the inner pushing tube 56 extends radially outwardly from the top of the inner pushing tube 56 (FIG. 6). The first flange 60 has a convexly shaped lower end. The first flange 60 includes four threaded bores 62 that extend down from the top of the first flange 60. The bores 62 are equally spaced around the first flange at ninety degrees between adjacent bores 62. Each bore 62 is sized to receive a connecting bolt 48 (FIG. 7) and bolt 68 (FIG. 8). Each bore 62 includes an upper portion 64 and a lower portion 66 (FIG. 12). The upper portion 64 is conically shaped and flares outwardly in the upward direction. The upper portion 64 is sized and shaped to match that of a head 67 of a connecting bolt 68. The lower portion 66 extends downwardly from the upper portion 64. The lower portion 66 is threaded with a diameter that is the same as the diameter of a threaded shank 70 of the connecting bolt 68. An inner surface 72 of the inner pushing tube 56 tapers toward its lower end to form a beveled tip 74.

The outer pushing tube 58 (FIG. 6) includes a second flange 76 integrally formed in one piece with the top of the outer pushing tube 58. The top of the second flange 76 is concaved to fittingly receive the convex lower end of the first flange 60 to help prevent lateral movement of the flanges with respect to each other. The second flange 76 extends radially inwardly from the top of the outer pushing tube 58. The second flange 76 includes four threaded bores 78 that extend down from the top of the second flange 76. The bores 78 are equally spaced around the second flange 76 at ninety degrees between adjacent bores 78. Each bore 78 is sized at the same diameter of the shank 70 of the connecting bolt 68 for threadily receiving the threaded shank 70. The outer surface 79 of the outer pushing tube 58 tapers toward its lower end to form a beveled tip 82.

When the inner and outer pushing tubes 56, 58 are assembled to together, the first flange 60 is positioned above and overlaps the second flange 76 such that the bores 62 of the first flange 60 are aligned with the bores 78 of the second flange 76. The threads of the connecting bolts 68 threadily engage the threads in the lower bore portions 66 and bores 78 to connect the pushing tubes 56, 58 to each other. The heads 67 of the connecting bolts 68 are seated in the upper portion 64 of the bore 62 and are located below the top surface of the inner pushing tube 56 so as to provide the uniform transfer of compaction load from a vibratory roller drum 24 to the testing sampler assembly 30 during compaction. The inner and outer pushing tubes 56, 58 remain connected during the entire compaction process. The diameter of outer tube 58 is larger than diameter of the inner pushing tube 56.

The bores 62, 78, 46 of the respective first flange 60, second flange 76, and stationary tube 32 have diameters that are sized to match the diameters of a threaded end 80 of the single lifting handle 50, the connecting bolt 48 and a single square rod 110. The connecting bolts 68 are generally made of suitable high strength material.

As seen in FIGS. 2, 6, and 12-15, the stationary tube 32 is positioned between the inner and outer pushing tubes 56, 58. The difference between diameters of the inner and outer pushing tubes 56, 58 is equal to a thickness of the stationary tube 32 as illustrated in the figures. Thus, the surfaces 81, 84 of the inner and outer pushing tubes 56, 58 facing the surface 86 of the stationary tube 32 form a tight contacting fit with the exterior surface 86 of the stationary tube 32 to prevent RCC paste from entering between the pushing tubes 56, 58 and stationary tube 32 that could interfere with a free sinking of the pushing tubes 56, 58. As seen in FIGS. 6 and 12-15, a compressible-rebound ring 88 is placed on the top of stationary tube 32, as a precaution, to protect threaded bores 46 and to prevent damage to the beveled tips 74, 82 of the pushing tubes 56, 58 in case of excessive compression when penetration of the firm base 22 may occur.

Since the pushing tubes 56, 58 are embedded into RCC lift 20 and thus, are an integral part of the RCC lift 20, they will sink at the same rate as the compression rate of the RCC core sample 38 inside the testing sampler assembly 30 and the loose RCC lift 20 around the testing sampler assembly 30. Moreover, the tips 74, 82 of the pushing tubes 56, 58 together with the RCC core sample 38 will sink at an equal increment as the vertical volume change of RCC core sample 38 and loose RCC lift 20 under the same applied vertical compaction load. Nonetheless, beveled tips 74, 82 of both tubes minimize lateral displacement of RCC aggregate and reduce downward resistance along the sliding surfaces of the stationary tube 32 when the pushing tubes 56, 58 are subjected to sinking by the compaction effort of the vibratory roller 24. In an alternative arrangement, the pushing tube assembly 54 may be formed in one piece or comprise of one tube.

Referring to FIG. 12, the RCC core sample 38 is surrounded by the inner pushing tube and has a diameter that is equal to the inside diameter of the inner pushing tube. Referring to FIGS. 2 and 12, plastic drainage-divider membranes 90 are used for drainage and to divide the RCC core sample 38 into as many smaller core sample portions 41, 43, 45, and 47 (FIG. 12) as necessary for laboratory testing. Each drainage-divider membrane 90 is porous and contains small holes, which will equalize the pore-water pressure in the RCC core sample 38 above and below the membrane 90, during compaction process. The open top of the RCC core sample 38 will allow air to escape from the core sample 38 during compaction.

Bonding cement paste 92 (FIG. 13) can also be placed within the RCC core sample 38, at various depths, in order to evaluate real time bonding strength within the newly placed RCC lift 20, at given depths below compaction surface, elapsed time after mixing, placement etc. A portion of the RCC core sample 38 that contains bonding surface may be tested in the laboratory to obtain actual bond strength along such a contact surface.

Figure 9:
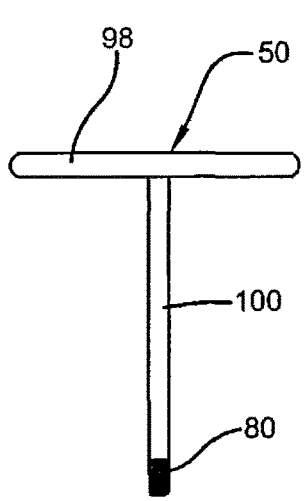
FIG. 9 shows a side plan view of an alternative lifting handle for the compaction testing sampler assembly.
Figure 11:
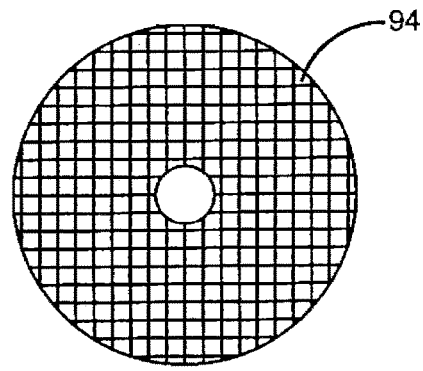
FIG. 11 shows a top plan view of the geo grid mesh of the compaction sampler assembly of FIG. 2.

As depicted in FIGS. 2 and 11, a geo-grid mesh 94 having a three foot diameter may be placed at the grade surface of loose RCC lift 20 around the top of the testing sampler assembly 30 to minimize shifting and tilting of the testing sampler assembly 30 by a vibratory roller 24 drum during the compaction process. Alternatively, the geo-grid mesh 94 or another geo-grid mesh 94 may be placed around the middle level of the testing sampler assembly 30 (FIG. 2). The additional geo-grid mesh 94 at the middle level of the testing sampler assembly further minimizes shifting and tilting of the testing sampler assembly 30 during the compaction process. Referring to FIG. 9, the single lifting handle 50 generally includes a head 98 and a shaft 100 extending from the center of the head 98. The shaft 100 includes the threaded end 80 that may threadily engage a threaded bore 46 in the stationary tube 32, a threaded lower portion 66 of the bore 62 in the first flange 60, or a threaded bore 78 in the second flange 76.

In an alternative arrangement as seen in FIG. 2, the threaded end 80 may engage a threaded hole 102 in the center of a cross-shaped bracket 104 attached to the inner pushing tube 56. Specifically, four shaped holes 106 are formed in the ends of four legs 108 forming the cross of the bracket 104. Four rods 110 are inserted into the holes 106. The rods 110 have a portion 112 that is square shaped in cross section that extends through the holes 106 of the bracket 104 and the bores 62, 78, 46 of the inner pushing tube 56, outer pushing 58, and stationary tube 32. Each rod includes a threaded lower end 118 for selectively threadily securing the rod to the pushing tubes 56, 58 and stationary tube 32. Nuts 114 are threadily secured at a threaded top end 116 of the rods 110 to secure the bracket 104 to the rods 110.

Figure 10:
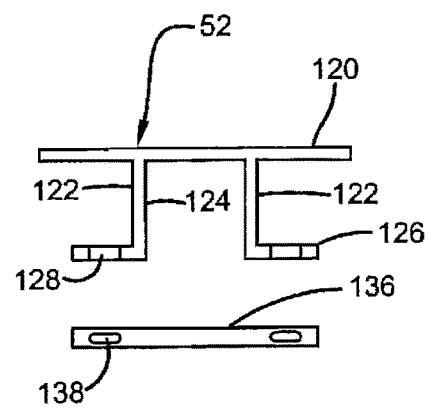
FIG. 10 shows a side sectional exploded view of another alternative lifting handle and related portion of the compaction testing sampler assembly.

FIG. 10 shows the double lifting handle 52, which alternatively may be used instead of the single lifting handle 50. The double lifting handle 52 includes a head portion 120 and a pair of L-shaped brackets 122. Each of the brackets 122 includes a proximal leg 124 that extends perpendicular from the head 120 and a distal leg 126 that extends radially outward from the proximal leg 124. Oval holes 128 are formed near the free ends of the distal legs 126 for receiving the bolts 48. A wrench 140 (FIG. 2) such as a French wrench may be used to tighten and loosen the bolts 48 or rods 110.

In addition, any other lifting method, equivalent and equal, mechanical or hand operated can be used to lift embedded tubes from the compacted RCC lift. The stationary tube 32 is typically three fourths of an inch thick and has a height that is equal to twice the inside diameter of the stationary tube 32.

Preparation of the Test Site and In-Situ Setting of RCC Compaction Testing Sampler Assembly The following is the preparation procedure for setting the in-situ RCC testing sampler assembly 30, which does not contain a previously compacted RCC core sample 37 with bonding surface at the bottom of stationary tube 32. The following steps shall be included in the preparation and setting procedure of the in-situ RCC testing sampler assembly 30.

Figure 14:
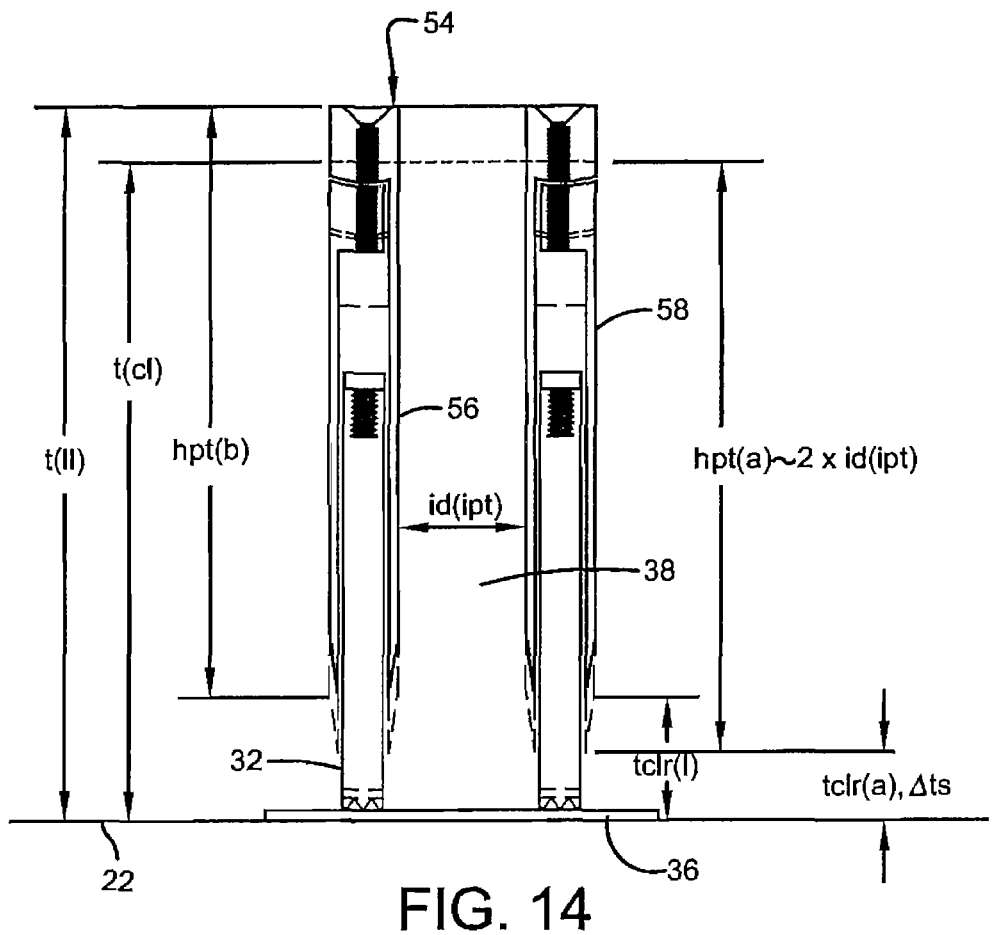
FIG. 14 shows a side sectional view of the testing sampler assembly with solid lines depicting the position of the testing sampler before compaction and phantom lines depicting the position of the testing sampler assembly after compaction.

Referring to FIG. 12, first, loose RCC lift 20 is spread with a bulldozer, over the previously compacted/old RCC lift, at required thickness, t(ll) (FIG. 14). The test location is then selected, and a cavity 130 (FIG. 12) is dug in the loose RCC lift 20 such that the bottom of cavity is at the surface of the previously compacted RCC lift 22. The cavity 130 is dug such that the diameter at the bottom of the dug cavity is slightly larger than the outside diameter of the testing sampler assembly 30 in order to provide clearance for adequate positioning and setting of the testing sampler assembly.

Any debris is removed from the dug cavity. The bottom of the cavity is trimmed and leveled with a small shovel in order to provide a good transfer of compaction load along the horizontal contact surface. The test location is marked at the bottom of the cavity and coordinates and elevation are obtained from the test location using a GPS system or other suitable system. The separation membrane 36 is placed on the bottom of the prepared cavity and centered over the marking of the proposed test location. The stationary tube 32 is placed on the separation membrane 36. The top of stationary tube 32 is tapped to set it firmly into the firm base 22 (FIGS. 2 and 4). The lower four inches of the stationary tube 32 is filled with RCC mix. The annular space around the outside surface of the stationary tube 32 is also filled to the same four inch level. During the filing, the RCC mix is placed in layers to prevent formation of voids. Then, the sliding contact surfaces between the stationary tube and the pushing tubes are greased. The compressible ring 88 is then placed on the top of stationary tube 32. The pushing tube assembly 54 is positioned vertically and slid over the vertical stationary tube 32 until the beveled tips 74, 82 rest upon the RCC mix that was filled inside and outside of the stationary tube 32. The level of the RCC mix is then raised or lower around the testing sampler assembly 30 until the top level of the surrounding loose RCC lift 20 is at the top of the pushing tube assembly 54. This permits the testing sampler assembly 30 with the loose RCC core sample 38 and the adjacent loose RCC lift 20 to compress equally under the full transfer of the applied compaction load to the RCC core sample 38 and surrounding RCC lift 20.

The annular space around the testing sampler assembly 30 is then hand filled with the RCC mix to its top and leveled with the top surface of the surrounding loose RCC lift. The RCC mix is then placed in thin layers around the testing sampler assembly 30 and compacted with a rod in order to eliminate any voids and to establish a tight contact between RCC mix and surfaces of the testing sampler assembly 30. The vertical alignment of the testing sampler assembly 30 is maintained during this process. The drainage-divider membrane 90 is inserted at the top of the lower RCC core sample inside stationary tube. The inside volume of the testing sampler assembly 30 is hand filled with RCC mix to its top. The drainage-divider membranes and/or bonding cement paste are inserted at desirable levels in order to divide the sample core into smaller sample cores for easier, faster and simultaneous laboratory testing for moisture, density compression strength and bond strength. The annular space around the testing sampler assembly 30 is hand filled with RCC mix to the top of the testing sampler assembly 30 and compacted as necessary in order to establish good contact with the testing sampler assembly 30, which will minimize its shifting and tilting during compaction. The testing sampler assembly 30 is check and adjusted as necessary to be in a vertical position. The geo-grid mesh is then placed at the ground level of the loose RCC lift, around the top of the testing sampler assembly 30, to position and secure it and to minimize shifting and tilting of the testing sampler assembly 30 during compaction process. The hole in the center of the mesh 94 is tightly positioned around the top of the testing sampler assembly 30. A second mesh may be placed around middle level of the testing sampler assembly 30, to even more minimize movement of the testing sampler assembly 30 during compaction.

Then, the coordinates and elevation of the testing sampler assembly 30 is obtain before compaction, and a plastic protection sheet 132 (FIG. 2) is placed over the embedded testing sampler assembly 30. One to two passes with bulldozer are then made, at a slow speed, in the same direction, over the embedded testing sampler assembly 30, to minimize its shifting and to achieve the similar compaction to a portion of RCC lift previously spread around the testing sampler assembly 30 and compacted by the bulldozer. The coordinates and elevation of the testing sampler assembly 30 are obtained again, and position of the testing sampler assembly 30 is check and adjusted as necessary to be in a vertical position. The RCC lift 20 is compacted together with the embedded testing sampler assembly 30 using a vibratory roller 24 as will be described below in further. The coordinates and elevation of the embedded testing sampler assembly 30 are obtained after a various number of passes to correlate number of passes and density. The obtained coordinates and elevations are used to calculate compression and shifting of the embedded testing sampler assembly 30 during compaction process.

Figure 13:
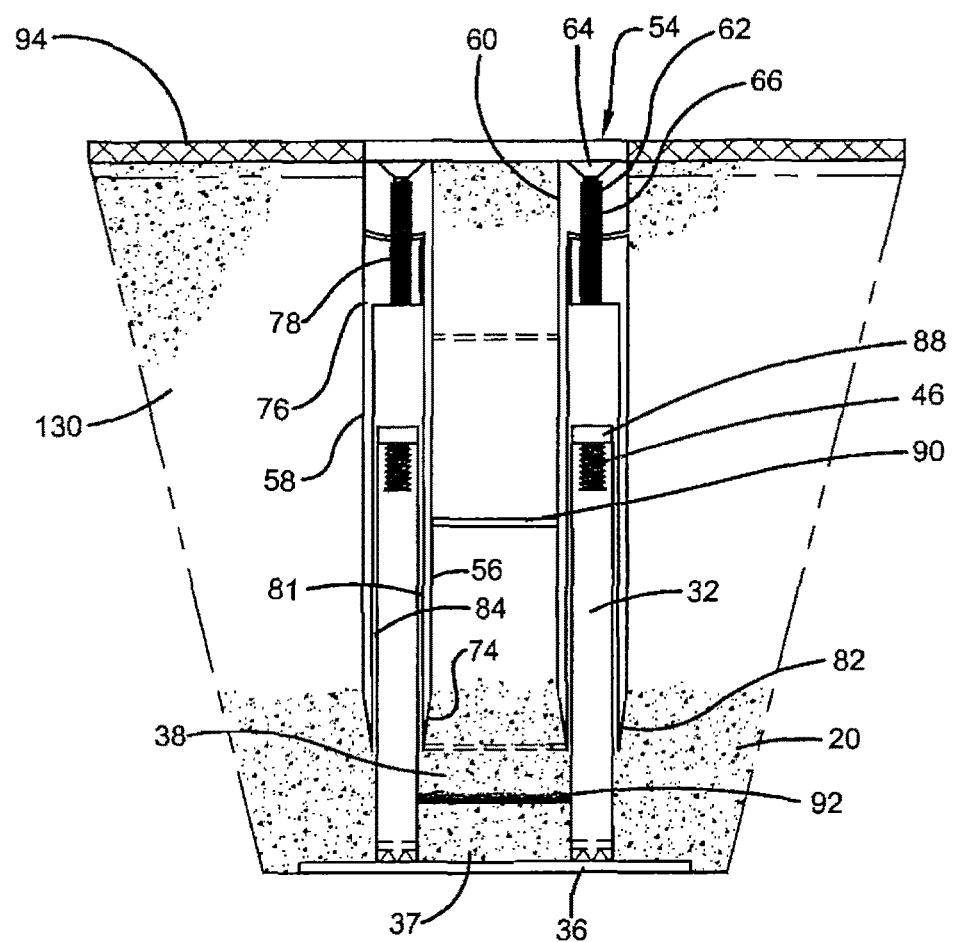
FIG. 13 shows side sectional view of the testing sampler assembly which contains an old RCC core sample at the bottom of the stationary tube.

The following is the preparation procedure for setting the in-situ RCC testing sampler assembly 30, which does contain a previously compacted RCC core sample 37 (FIG. 13) with bonding surface at the bottom of stationary tube 32. The following steps shall be included in the preparation and setting procedure of in-situ RCC compaction testing sampler assembly 30 to obtain bonding strength along the contact surface of an old previously compacted RCC core sample/lift and subsequently placed RCC mix, as shown in FIG. 13.

First, loose RCC lift 20 is spread with a bulldozer, over the previously compacted/old RCC lift, at required thickness t(ll) (FIG. 14). The test location is then selected, and a cavity 130 is dug in the loose RCC lift such that the bottom of cavity is at the surface of the previously compacted RCC lift 20. The cavity 130 is dug such that the diameter at the bottom of the dug cavity 130 is slightly larger than the outside diameter of the testing sampler assembly 30 in order to provide clearance for adequate positioning and setting of the testing sampler assembly 30.

Any debris is removed from the dug cavity 130. The bottom of the cavity 130 is trimmed and leveled with a small shovel in order to provide a good transfer of compaction load along the horizontal contact surface. The test location is marked at the bottom of the cavity 130 and coordinates and elevation are obtained from the test location using a GPS system or other suitable system. The separation membrane 36 is removed from the top of the previously compacted RCC core sample 37 inside the stationary tube 32. The separation membrane 36 is placed on the bottom of the prepared cavity 130 and centered over the marking of the proposed test location. The stationary tube 32 with the old compacted core sample 37 is placed on the separation membrane 36. The top of stationary tube 32 is tapped to set it firmly into the firm base 22 (FIG. 2).

The annular space around the outside surface of the stationary tube 32 is also filled to the level equal to twice the thickness of the compacted core sample 37. During the filing, the RCC mix is placed in layers to prevent formation of voids. The thickness can be adjusted to meet the required overall thickness of the sample to be used for determination of bond strength.

Then, the sliding contact surfaces between the stationary tube 32 and the pushing tubes 56, 58 are greased. The compressible ring 88 is then placed on the top of stationary tube 32. The pushing tube assembly 54 is positioned vertically and slid over the vertical stationary tube 32 until the beveled tips 74, 82 rest upon RCC mix that was filled inside and outside of the stationary tube 32. The level of the RCC mix is then raised or lowered around the testing sampler assembly 30 until the top level of the surrounding loose RCC lift is at the top of pushing tubes assembly 54. This permits the testing sampler assembly 30 with the loose RCC core sample and the adjacent loose RCC lift to compress equally under the full transfer of the applied compaction load to the RCC core sample 38 and surrounding RCC lift 20. The annular space around the pushing tubes assembly 54 is then hand filled with the RCC mix to the top surface of the surrounding loose RCC lift 20. The RCC mix is then placed in thin layers around the testing sampler assembly 30 and compacted with a rod in order to eliminate any voids and to establish a tight contact between RCC mix and surfaces of the testing sampler assembly 30. The vertical alignment of the testing sampler assembly 30 is maintained during this process.

Bonding cement paste is then spread over the top surface of the previously compacted RCC core sample 37 located at the bottom of the stationary tube 32. Immediately following spreading of the cement paste, the inner pushing tube 56 is hand filled with a new RCC mix to a height equal to the height of RCC fill outside of the stationary tube 32, which height is approximately equal to two times the height of the previously compacted RCC sample at the bottom of the stationary tube 32. A new drainage-divider membrane 90 is placed at the top of the new fill.

The rest of the inner pushing tube 56 is hand filled with RCC mix to its top. The drainage-divider membranes 90 and/or bonding cement paste are inserted at desirable levels in order to divide the sample core into smaller cores for easier, faster and simultaneous laboratory testing for moisture, density compression strength and bond strength. Placing cement paste between fresh RCC to obtain its bonding strength could be used for comparison with bonding strength determined at the surface of previously compacted and the new RCC. This will allow the operator to establish if there is any difference between these two values, which could be related to an elapsed time between testing and compaction of the previously compacted RCC lift.

The testing sampler assembly 30 is checked and adjusted as necessary to be in a vertical position. The geo-grid mesh 94 is then placed at the ground level of the loose RCC lift, around the top of the testing sampler assembly 30, to position and secure it and to minimize shifting and tilting of the testing sampler assembly 30 during compaction process. The diameter of the geo-grid mesh 94 can be adjusted to the diameter of the dug hole at the level of placement. The hole in the center of the mesh 94 is tightly positioned around the top of the testing sampler assembly 30. A second mesh 94 may be placed around middle level of the testing sampler assembly 30, to even more minimize movement of the testing sampler assembly 30 during compaction.

Then, the coordinates and elevation of the testing sampler assembly 30 are obtained before compaction, and a plastic protection sheet 132 is placed over the embedded testing sampler assembly 30. One to two passes with bulldozer are then made, at a slow speed, in the same direction, over the embedded testing sampler assembly 30, to minimize its shifting and to achieve the similar compaction to a portion of RCC lift 20 previously spread around testing sampler assembly 30 and compacted by the bulldozer. The coordinates and elevation of the testing sampler assembly 30 are obtained again, and position of the testing sampler assembly 30 is checked and adjusted as necessary to be in a vertical position. The RCC lift 20 is compacted together with the embedded testing sampler assembly 30 using a vibratory roller 24 as will be described below in further. The coordinates and elevation of the embedded testing sampler assembly 30 are obtained after a various number of passes to correlate number of passes and density. The obtained coordinates and elevations are used to calculate compression and shifting of embedded testing sampler assembly 30 during compaction process.

Dimensions and arrangement of the testing sampler assembly 30, before and after compaction, is shown in FIG. 14. The testing sampler assembly 30 height and diameter are dependent on the set thickness of loose RCC Lift 20, t(ll). The laboratory testing procedure to obtain compressive strength from the core samples requires that the ratio of the compacted height of the core sample, hpt(a), to its compacted diameter id(ipt) is maintained close to: hpt(a)=2id (ipt). In addition, the thickness of RCC loose lift t(ll) must always be greater than a constant height of the pushing tube assembly hpt(b) before compaction or hpt(a) after compaction. The difference between the value t(ll) and a constant height of the pushing tube assembly hpt(b) or hpt(a) is equal to the tip clearance of the pushing tubes above the firm base 22 before compaction tclr(b), which always must be greater than expected compression of loose RCC lift (Ats) in order to prevent penetration of the pushing tubes' tips 74, 82 into the firm base 22. Tip clearance tclr(b) before compaction, in this application was set to be four inches, as shown in FIG. 14. This dimension will assure that the pushing tubes' tip clearance after compaction tclr(a) will always be greater than zero, so that the compaction force applied to the testing sampler assembly 30 assembly, by a vibratory roller is always transferred to, and carried by the RCC core sample 38 inside the testing sampler assembly 30. Thus, the portion of the RCC core sample 38 in the inner pushing tube 56 as well as the portion of the RCC core sample 38 below the drainage-divider membrane 90, in the stationary tube 32 will compress freely, at the same rate as the loose RCC lift 20 around the testing sampler assembly 30, without the tips of the pushing tubes penetrating the firm base. Therefore, to make sure that this requirement is always satisfied the thickness of loose RCC lift t(ll) should not be equal to a constant height of the pushing tubes h(pt), because in such a case the tip clearance before compaction tclr(b) will be equal to zero and no sinking of the pushing tubes (i.e. compression of RCC core sample) inside the inner pushing tube will be possible without the tips of pushing tubes penetrating the firm base.

In fact, this value should be adjusted, after a more accurate value is determined by pilot testing before construction.

Compaction of Loose RCC Lift Together with the Embedded RCC Testing Sampler Assembly Simultaneous compaction of the loose RCC lift 20 and embedded testing sampler assembly 30 is cautiously conducted. The compaction is performed back and forth over the same perpendicular compaction paths. The critical first pass is made at a slow passing speed and with no vibration applied by the vibratory roller drum 24. The slow passing speed without the vibrations of the vibratory roller drum considerably reduces the excessive initial shifting and tilting of the testing sampler assembly 30 from its original vertical position. The movements of the vibratory roller 24 drum back and forth over the same compaction path results in a reduction of the lateral movement of the testing sampler assembly 30. The compaction continues over the same footprint for at least three passes. The direction of compaction may be changed after three passes. However, a sharp turning of the drum at, and in the near vicinity of the embedded testing sampler assembly 30 should be avoided, because it may result in an excessive disturbance of the testing sampler assembly 30. Vibrations produced by the vibratory drum minimize friction between the outer pushing tube 58 and RCC mix of the testing sampler assembly 30. The vibrations also enhance the downward movement of the inner and outer pushing tubes 56, 58.

The rate of compression for the testing sampler assembly 30 with the RCC core sample 38 and adjacent RCC lift will be simultaneous and equal. However, a small variation is always possible, due to variation of the initial densities and moisture contents among the RCC core samples and the adjacent RCC lift. Preferably, the testing sampler assembly 30 is kept in its vertical position, during compaction to maintain both the diameter and cylindrical shape of the sample. In order to stabilize the testing sampler assembly 30, the three foot diameter geo-grid mesh 94 with a center hole equal to the outer diameter of the testing sampler assembly 30 is placed around the testing sampler assembly 30 at the ground level and middle level if necessary.

The restraining effect of the geo grid mesh minimizes the shifting and tilting of the testing sampler assembly 30 during compaction. Furthermore, the impact and vibrations from a drum of the vibratory roller 24 that are applied simultaneously to the top of testing sampler assembly 30, the sample 38 inside the testing sampler assembly 30, and the surface of the adjacent RCC lift 20 always are the same, at a given testing location. In fact, when such compression load is applied simultaneously to all three, it will cause an equal compressive motion between lift firm base 22 and the top surface at which the compaction load is applied, as long as their initial densities are the same. The initial density of the RCC sample 38 and the RCC lift 20 at the testing locations are expected to be the same, as well as their compression rates, although some small variations are possible. In other words, a sinking rate of the embedded pushing tubes, when pushed deeper into the RCC lift 20 with a vibratory roller 24, along the vertical sliding surfaces of the stationary tube 32 is equal to the compression rate of the RCC sample inside the pushing tubes and RCC lift around the testing sampler assembly 30.

The pushing tubes 56, 58, RCC sample 38, and RCC lift 20 will sink and compact together, under the same compaction force of a vibratory roller 24 that is applied under the lift's same confined pressure, resulting in only the vertical adjustment of aggregate particles within the RCC material. Thus, simultaneous sinking of the pushing tubes 56, 58 will be equal to the vertical adjustment of aggregate particles within the loose RCC lift. The movement of the pushing tube assembly 54 is illustrated in FIG. 14 with the solid lines of the pushing tube assembly 54 showing the position of the pushing tube assembly 54 in the uncompacted position before compaction of the RCC lift 20 and the phantom lines showing the position of the pushing tube assembly 54 in position after compaction of the RCC lift 20. The lateral displacement of the RCC material by the beveled tips of the pushing tubes will be negligible, and should not have any adverse effect on the compaction process.

The Compaction Ratio (crt) for the RCC sample and the RCC lift is defined as the ratio of compacted RCC thickness t(cl) to RCC loose thickness t(ll) as depicted in FIG. 14. An equal Compaction Ratio (crt) for the RCC sample and RCC lift would indicate that both of them were compacted under the same confined and loading conditions. Though, the difference in (crt) value for the RCC sample and RCC lift is possible, due to possible variation of lateral restraining, initial density and the size of RCC aggregate. The difference in (crt) value, at these two adjacent locations, is expected to be small. It is important to note that steady downward force of vibratory roller drum is applied to the testing sampler assembly 30 only during passing of the drum. Therefore, a continuous motion of the testing sampler assembly 30 during compaction process is not obtained. This should not have effect on the results of the tests. The effect of a large size aggregate will be reduced by careful packing and tapping of RCC material adjacent to testing sampler assembly 30's surfaces. Furthermore its compaction with the vibratory roller fills any void with a finer RCC mix and paste. In addition, it is important to establish a full contact along the outside surfaces of the testing sampler assembly 30 in order to minimize its shifting and tilting during compaction as well as the filling with cement paste the space between these surfaces.

Retrieval of In-Situ Embedded RCC Compaction Testing Sampler Assembly from Compacted RCC Lift Retrieval of the embedded testing sampler assembly 30 from the compacted RCC lift may be accomplished by the use of the single lifting handle 50, double lifting handle 52 or other suitable lifting device, depending on the weight or size of the testing sampler assembly 30. For an easier lifting of each pushing tube out of the compacted RCC lift 20, the tubes may be rotated, simultaneously with the exertion of an upward force to break any bond adjacent to the compacted RCC lift and the greased vertical outside surface of the outer pushing and stationary tubes as well as along the horizontal surface of drainage-divider membrane.

Figure 15:
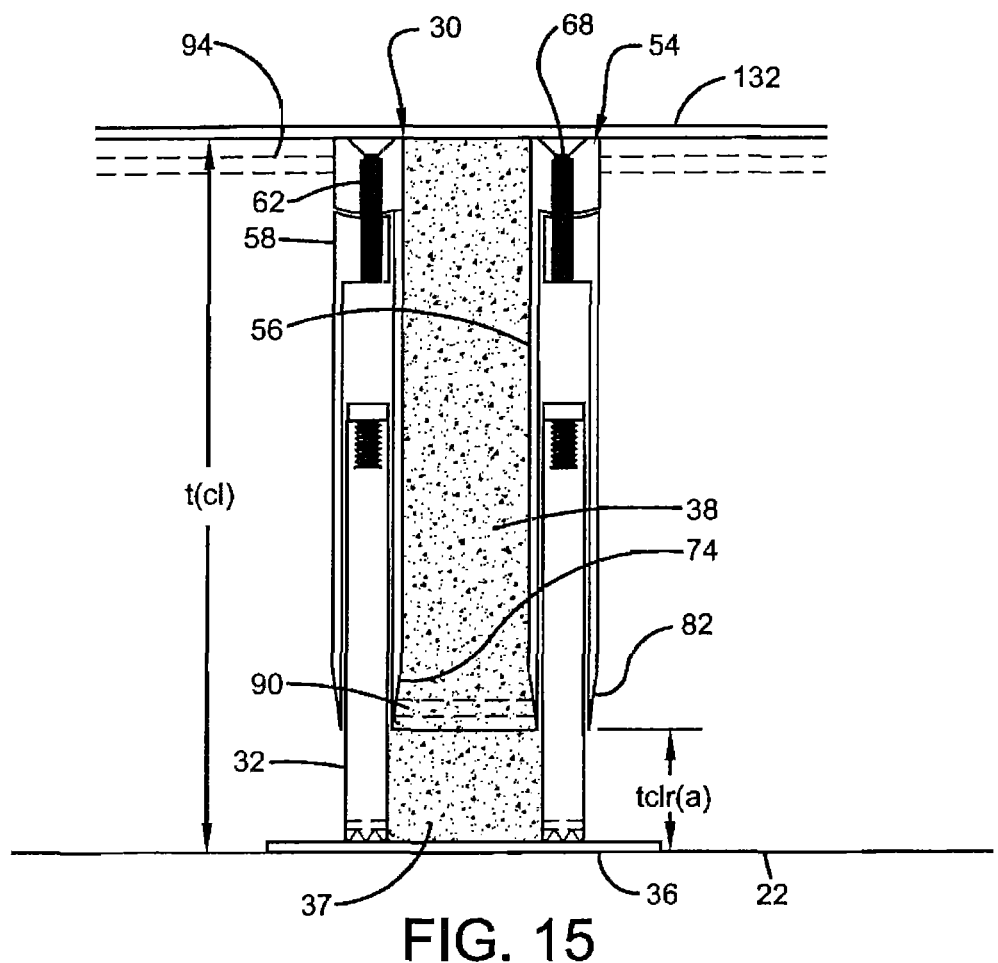
FIG. 15 shows a side sectional view of the testing sampler assembly embedded in compact RCC lift for retrieval.
Figure 16:
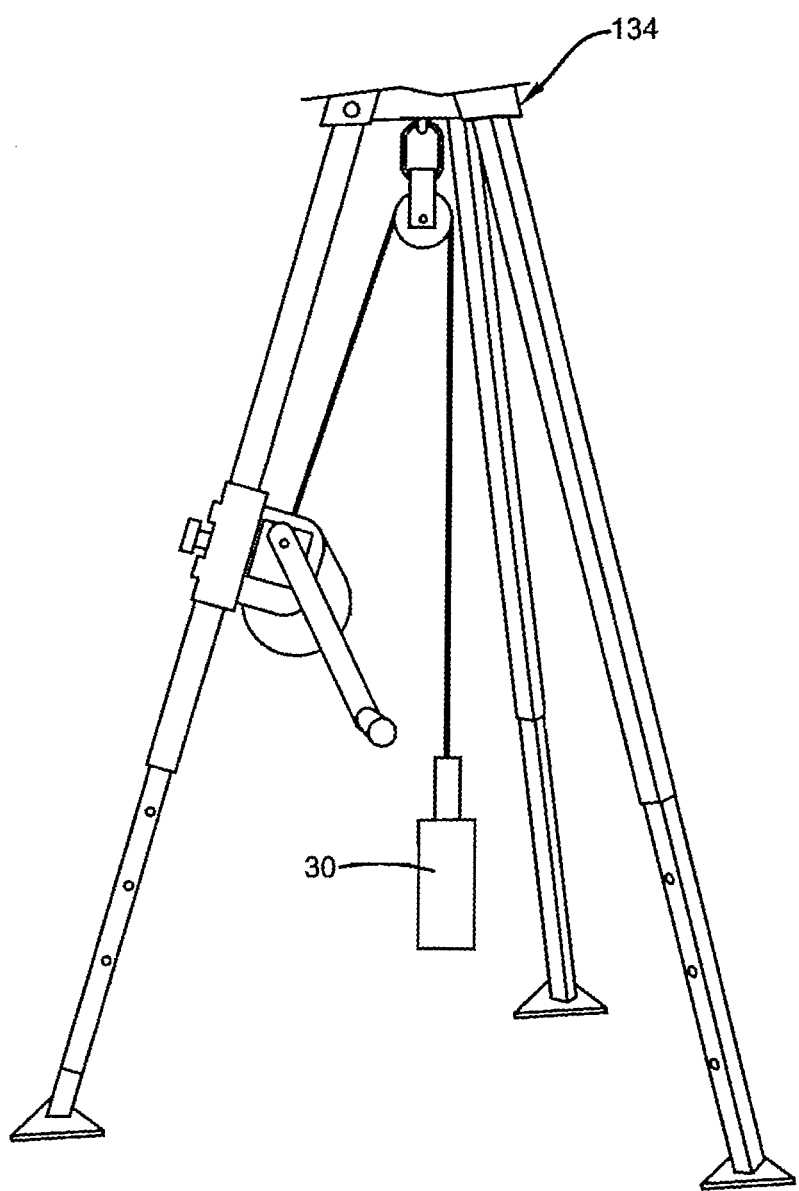
FIG. 16 shows a lifting mechanism for the testing sampler assembly.

Retrieving the embedded RCC testing sampler assembly 30 from the compacted RCC lift is discussed as follows with reference to FIG. 15. The plastic protection cover 132 is removed from the top of the embedded testing sampler assembly 30. The annular space between the geo-grid mesh opening and the outside surface of the testing sampler assembly 30 is cleaned for easier lifting. The geo-grid mesh 94 may be cut and removed as necessary. The connecting bolts 68 are then removed from the top of the pushing tubes 56, 58. A single lifting handle 50 (FIG. 9) is threadily secured via its threaded end 80 into one of the threaded bores 62 in the inner pushing tube 56 (FIG. 6). Additional lifting handles may also be threadily secured in the other threaded bores of the inner pushing tube. Alternatively, as seen in FIG. 2, the single lifting handle 50 may be threadily secured via its threaded end 80 into the center hole 102 of the bracket 104. The bracket 104 may be secured to the inner pushing tube by the rods 110 extending through the holes 106 and secured or threaded into the bores 62 via its threaded end 118. The bracket 104 is secured with nuts 114 threaded on the top ends 116 of the rods and with the nuts 114 engaging the top surface of the bracket 104.

Alternatively, the double lifting handle 52 (FIG. 10) may be attached to respective bores 62 in the inner pushing tube 56. Specifically, a bracket 136 with holes 138 (FIG. 10) are aligned over opposite bores 62 and connecting bolts 48 (FIG. 7) are then threaded into their respective holes 128, 138 and bores 62. In another alternative arrangement, the double lifting handle 52 may be secured to the inner pushing tube 56 using only two rods 110 and two nuts 114. Specifically, the double lifting handle 52 is secured to the inner pushing tube 56 by the rods 110 extending through the holes 128 and threaded into the bores 62 via its threaded end 118 and with nuts 114 threaded on the top ends 116 of the rods and engaging the top surface of the distal leg 126 (FIG. 10). After the single lifting handle(s) or double lifting handle is secured to the inner pushing tube 56, the lifting handle is rotated and lifted to lift the inner pushing tube 56 with the compacted RCC sample 38 inside. The sample 38 is stored for further testing.

Then, the single lifting handle(s) or double lifting handle is secured to the outer pushing tube 58 and rotated and lifted to lift the outer pushing tube 58 in a similar fashion as that done for the inner pushing tube 56. The compression-rebounding ring 88 is then removed. The single lifting handle, or double lifting handle, or bracket 104 is secured to the top of the stationary tube 32 with rods 110 and nuts 114 and rotated and lifted to lift the stationary tube 32 with the RCC core sample 37 (with or without cement paste bond surface). It should be noted that the compaction forces against the inner wall surface of the inner pushing tube 56 and inner wall surface of the stationary tube 32 provide sufficient frictional force to retain the compacted samples 37, 38 to the tubes during lifting of the tubes out of the RCC lift 20 for testing. During rotation and rocking of the inner pushing tube 56 and stationary tube 32 to loosen them up from the adjacent RCC lift, the samples inside both tubes will remain stationary and bond to retain them in the tubes.

Figure 17:
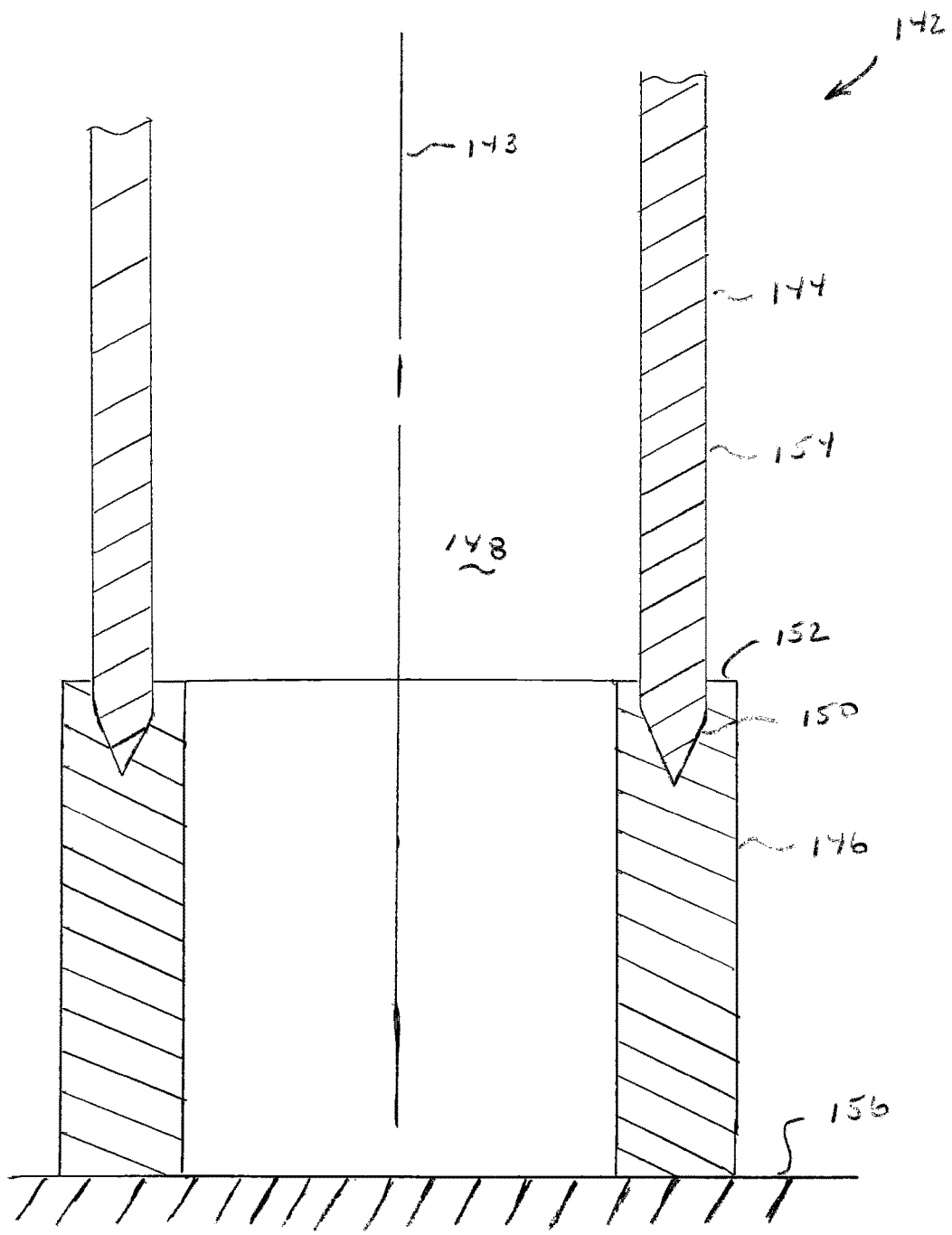
FIG. 17 is a cross-sectional view of an alternative embodiment of a concrete testing sampler.

Retrieving the embedded RCC testing sampler assembly 30 from the compacted RCC lift which does not contain an old RCC core sample at the bottom of the stationary tube as shown in FIG. 12 is similar to that described above except that the stationary tube 32 would contain the RCC sample portion 47. Optionally, an inside lip may be provided on the lower end of the stationary tube to further help retain the RCC sample portions to the tubes. The retrieved RCC sample portions 41, 43, 45, 47 (FIG. 12) are used for laboratory testing to determine water content, density, bond strength and compressive strength for the rapidly placed and compacted RCC lifts, during construction. Alternatively or additionally, a tripod hoist 134 may be used for lifting the testing sampler assembly 30 from compacted RCC lift as seen in FIG. 17.

Although description of the testing sampler assembly 30 contains much specificity, these should not be construed as limiting the scope of the testing sampler assembly 30 but as merely providing illustrations of some of the preferred schemes of the testing sampler assembly 30. For example, the testing sampler assembly 30 can have other combinations of stationary tube and pushing tubes as long as one slides within the other to allow adjustment in the overall height of the testing sampler assembly 30 equal to the simultaneous compression of the RCC core sample inside the testing sampler assembly 30 and the RCC lift 20 adjacent to the testing sampler assembly 30 during the entire compaction process. Thus, the scope of the testing sampler assembly 30 should be determined by the appended claims and their legal equivalents, rather than by the example given.

This in-situ compaction RCC testing sampler assembly 30 can be set into the loose RCC lift easily and conveniently, and can be compacted together with the RCC sample as effectively as the loose RCC lift adjacent to the testing sampler assembly 30. The testing sampler assembly 30 can be retrieved from a compacted RCC lift just as easily, and without damage to the sample. Furthermore, the testing sampler assembly 30 has the additional advantages in that it allows a specified amount of the compaction energy-number of passes to be applied to the testing sampler assembly 30, pushing tubes, RCC core sample inside the inner pushing tube and the surface of the RCC lift adjacent to testing sampler assembly 30. As the pushing tubes are being pushed into the loose RCC lift, the same compaction energy of the compaction equipment is simultaneously transferred to the RCC core sample being compacted inside the testing sampler assembly 30. It can be used repeatedly, not only for compaction testing of RCC material but also for compaction testing of any other compactable material including: soils, bottom ash and fly ash.

Since the testing of each RCC lift and RCC lift compaction process occurs during construction, each compacted sample retrieved from the compacted RCC lift is obtained under the lift's in-situ identical compaction conditions. The all around in-situ confined pressure of the RCC lift, adjacent to the embedded testing sampler assembly 30 and the RCC core sample inside the testing sampler assembly 30, is an integral part of the compaction process. Drainage and air escape is permitted during simultaneous compaction of RCC lift and RCC core sample inside testing sampler assembly 30. The RCC core sample inside the testing sampler assembly 30 is compacted simultaneously and effectively as the RCC loose lift adjacent to the testing sampler assembly 30. Consistency in obtained results is achieved, because the testing is always performed under the actual field conditions. The tubes of the testing sampler assembly can be easily redesigned for the market from the tubes which are already commercially available. The testing sampler assembly 30 may be transported and operated by one person, at the low operating cost, rapid field and laboratory testing, and timely use of test results. The testing sampler assembly 30 is simple to use, inexpensive to manufacture and can be used repeatedly.

Retrieved samples from the compacted RCC lifts can be tested immediately after compaction, to obtain reliable densities and moistures for the RCC lift. Any disagreement of these values with the values required by the specifications can be corrected before a subsequent RCC lift is placed. The continuity of the proposed direct testing method and "as you go" monitoring represents considerable improvement over the indirect testing methods currently in use. Retrieved sample can also be tested to obtain a bonding strength between compacted RCC lifts.

Specific disadvantages of existing testing devices will be eliminated; including dislocation of the larger size aggregate by the nuclear gauge probe; operator dependent compaction energy during preparation of test cylinders and the volume error during test by the sand cone method. Also, the cost of plastic cylinders currently required for each new tests will be avoided.

FIG. 17 shows an alternative exemplary arrangement of a testing sampler 142. FIG. 17 shows a portion of the testing sampler below the top area thereof and without the sample material therein. The exemplary testing sampler 142 includes a tube 144 and a tube 146 each of which extend in concentric relation about an axis 143. In the exemplary arrangement tube 144 is comprised of a relatively rigid material such as steel. The exemplary tube 146 is comprised of a relatively deformable material, such as a plastic material. In the exemplary arrangement tubes 144 and 146 bound an interior area 148 in which a sample of the concrete lift is housed during use. The interior area may also include horizontally extending separators, sample dividers, cement paste layers or other items that are included in a test sample as previously discussed. In the exemplary arrangement tube 144 includes an annular pointed tip 150. In the exemplary arrangement the pointed tip is initially embedded in the tube 146 somewhat below an upper surface 152 thereof. In the exemplary arrangement an outer annular surface 154 of tube 144 is coated with a nonstick coating. In exemplary arrangements the nonstick coating may comprise a layer of tetrafluoroethylene (TFE). Of course in other embodiments other materials may be used.

In the use of the exemplary sampler 142 shown in FIG. 17, the lower end of the tube 146 is supported on a base 156. The base may comprise the upper surface of the previously roller compressed concrete lift or other surface on which the roller compacted concrete layer is to be deposited. As in the previously discussed examples, the area surrounding the testing sampler 142 and the interior area 148 are filled with the loose compactable concrete lift. One or more layers of geo grid mesh may be placed adjacent to the top area and/or vertically intermediate areas of the tubes to provide enhanced lateral stability. The concrete lift is then roller compacted in a manner like that previously discussed. The roller compaction results in relative vertical movement of tubes 144 and 146 so as to compact the sample located in the interior area 148.

During compaction in use of the exemplary embodiment, the pointed tip 150 of tube 144 moves downward relative to the upper surface 152 of tube 146. The plastic deformable material of which tube 146 is comprised, is deformed and penetrated by the tip 150. In the exemplary arrangement the tip 150 is moved downwardly during compaction toward the base 156. Once compaction is complete, tube 144 is extracted by being removed upwardly from the compacted concrete lift along with the compacted sample therein. In some exemplary arrangements the extraction of the upper tube 144 is operative to bring with it not only the sample but also at least a portion of tube 146. In some embodiments tube 146 is configured to fracture vertically along the annular line of penetration such that the portion of tube 146 which extends radially inward of the annular tip 150 is extracted with the tube 144. In other arrangements the inner diameter of the tube 146 may be sufficiently low in friction or a lubricating material may be applied such that the sample portion therein is extracted while the deformed tube 146 remains in place. In some arrangements a horizontal separator may be placed in the interior area at about the same level as the upper surface 152 of the tube 146 so that when the tube 144 is extracted only the sample material above the separator is removed with the tube 144. Numerous different approaches may be taken in different exemplary embodiments.

Figure 18:
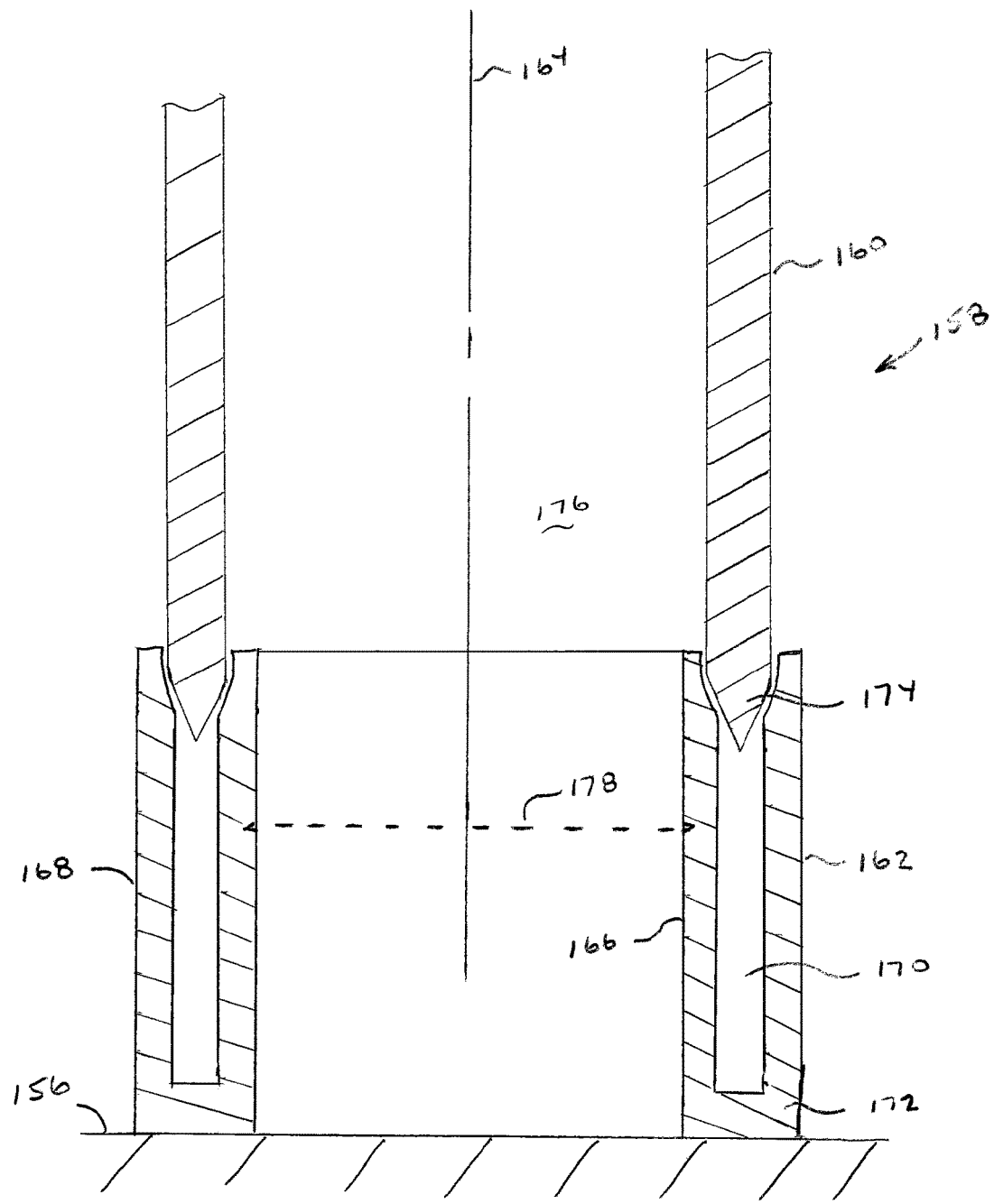
FIG. 18 is a cross-sectional view of another alternative embodiment of a concrete testing sampler.

FIG. 18 shows an alternative exemplary arrangement of a testing sampler 158. Sampler 158 includes a relatively rigid tube 160 and a tube 162 comprised of relatively softer deformable material. Tubes 160 and 162 extend in concentric relation about an axis 164. Tube 162 includes an inner annular ring 166 and an outer annular ring 168. Outer ring 168 is radially spaced from inner ring 166 so as to define an annular gap 170. An end portion 172 operatively connects the inner and outer rings.

Tube 160 includes an annular tip 174. In the exemplary arrangement tip 174 comprises a generally pointed annular tip that is configured to extend in the gap 170. In the exemplary arrangement the tip 174 is operative to move downward vertically in the gap 170 as shown in FIG. 18 during compaction of the concrete lift. With such movement of tube 160, at least one of the inner wall 166 and outer wall 168 deforms as the tube 160 moves further in the axial direction into the gap. In exemplary arrangements the tip moves into the gap during compaction of the concrete lift but does not reach the end portion 172. Of course this approach is exemplary and in other embodiments the end portion which connects the annular rings may be comprised of material that enables movement of the tip therein and deformation thereof during compaction.

In the exemplary arrangement once the compaction of the concrete lift is complete tube 160 is extracted from the compacted concrete lift by pulling the tube vertically upward. In the exemplary arrangement this causes the compacted sample located in the interior area 176 to be removed with the tube and available for testing. In some exemplary arrangements extraction of the tube 160 may also result in extraction of a portion of the deformable tube 162. Alternatively in some arrangements all or a portion of the deformable tube may remain embedded in the compacted concrete lift. Also in some arrangements a separator may be used to separate the portion of the sample that is removed from the portion that remains embedded with tube 162.

In some exemplary embodiments tube 162 may include annular fracture lines 178. In exemplary arrangements the fracture lines may comprise thinned or semi-perforated areas of the inner wall 166. Such fracture lines may be configured to fracture with inward defamation of the inner wall by movement of the tip 174 adjacent thereto. Alternatively or in addition such fracture lines may be configured to fracture when compacted sample material therein is pulled upwardly with upward movement of tube 160. In some exemplary arrangements, the inner ring 166 may include a plurality of axially disposed fracture lines so as to facilitate breakage of the annular inner wall and removal of the compacted sample material contained therein. Of course it should be understood that this approach is exemplary and in other embodiments other approaches may be used.

Figure 19:
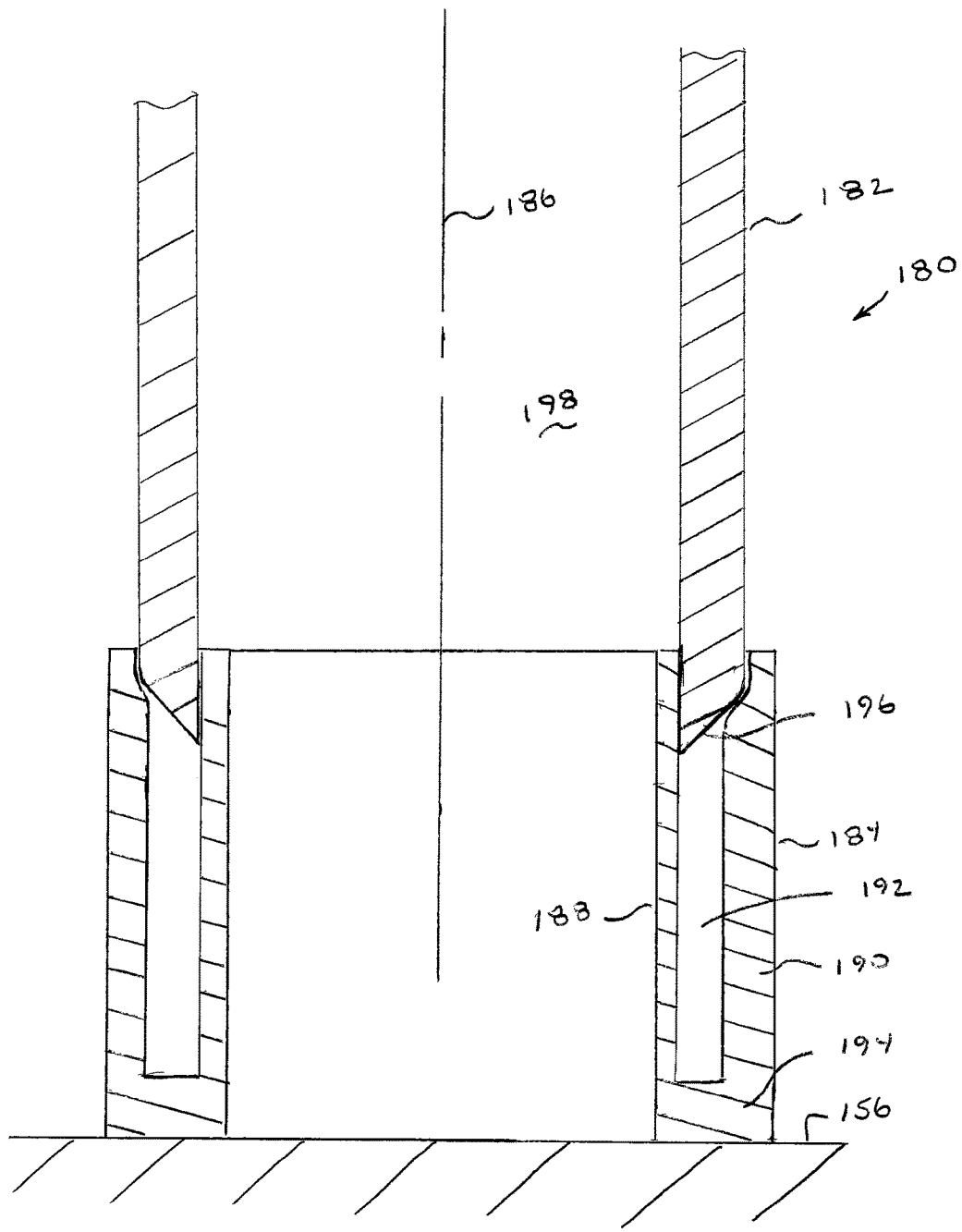
FIG. 19 is a cross-sectional view of another alternative embodiment of a concrete testing sampler.

FIG. 19 shows a further alternative arrangement of a concrete testing sampler 180. Sampler 180 includes a relatively rigid tube 182 and a deformable tube 184. Tubes 182 and 184 extend about a central axis 186. Deformable tube 184 includes an annular inner ring 188 and an annular outer ring 190. A radial gap 192 extends between the inner and outer rings. An end portion 194 is operative to connect the inner and outer rings of the tube 184.

In the exemplary arrangement tube 182 includes an outwardly beveled annular tip 196. Tip 196 is configured to extend in the gap 192. During compaction, a sample of the concrete lift extends in the interior area 198 of the tubes 182 and 184. During compaction tip 196 moves further axially into the gap 192 as the lift is compacted. In the exemplary embodiment tube 184 is deformed by the movement of the tip 196 in the gap. In the arrangement shown in FIG. 19, the tip is configured to more greatly deform the outer annular ring 190 than the inner annular ring 188 as the tubes 182 and 184 relatively move vertically due to compaction. In this exemplary arrangement minimizing the deflection of the inner ring may reduce radial compaction of the sample due to radial deformation of the interior area 198. Further, in some alternative arrangements the radial deformation of both the inner and outer rings may be minimal. Of course these approaches are exemplary and other embodiments other approaches may be used.

Although in the exemplary embodiments shown the deformable tube is positioned vertically below the more rigid tube, other arrangements may have different configurations. For example in some arrangements the deformable tube may vertically overlie the more rigid tube. In other arrangements the deformable tube may be positioned intermediate of a pair of more rigid tubes. Other arrangements may include a plurality of alternatively vertically arranged deformable tubes and rigid tubes. Numerous different arrangements may be utilized to achieve the principles as described herein. Also different arrangements may incorporate features from numerous different described embodiments.

Some arrangements may utilize different types of relatively rigid and deformable materials for the structures that contain the sample during compaction. For example, in some exemplary embodiments the relatively rigid tube may be comprised of a hard steel material or other metal or alloy. The deformable tube may be comprised of a plastic such as polypropylene or polyethylene. Also various lubrication materials or other coatings may be used to assure that the sample is compacted to the same extent as the surrounding material. Of course these materials are exemplary of the numerous different types of materials that may be utilized in connection with testing samplers for concrete lift.

Figure 20:
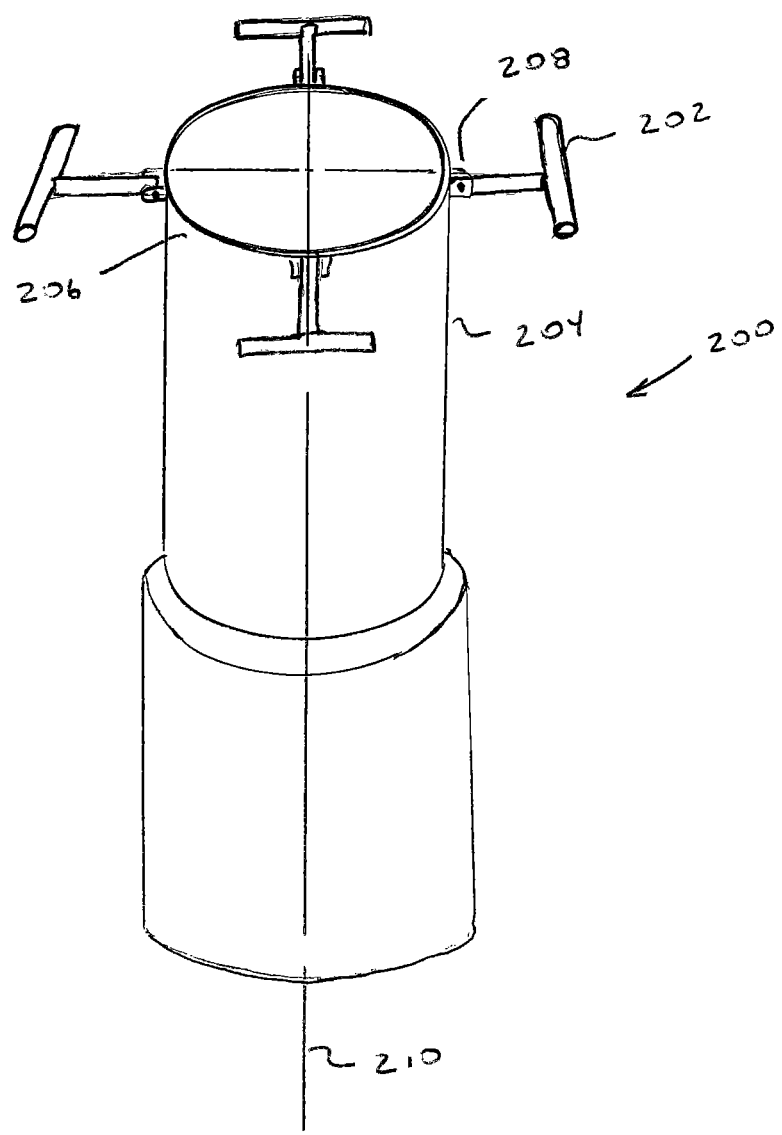
FIGS. 20-21 are perspective views of a concrete testing sampler with movable attached handles.

FIG. 20 shows an exemplary arrangement of a testing sampler 200. Testing sampler 200 may operate using the principles previously discussed. The exemplary sampler 200 includes a plurality of angularly spaced handles 202. Handles 202 are movably attached to the upper tube 204 in an upper annular area 206 thereof. In the exemplary arrangement each of the handles is movably operatively connected to the upper area 206 through a respective pivot 208. Each pivot 208 enables the respective handle 202 to be moved between a position in which the handle extends generally perpendicular to a central axis 210 of the sampler as shown in FIG. 20, and the position shown in FIG. 21 in which each handle extends generally parallel to the axis. In some arrangements the handles can be moved further beyond the position parallel to the axis so the handles are positioned closer together above the sampler.

In an exemplary arrangement the sampler 200 may be positioned within the surrounding uncompacted concrete lift with the handles 202 extending generally perpendicular to the axis as shown in FIG. 20. In this arrangement the handles are engaged with and are at the level of the upper surface of the concrete lift. During roller compaction the handles remain extended and are moved downward with the upper level of the concrete lift. The T-shaped configuration of the exemplary handles enable such handles to be embedded in the upper surface of the compacted material. In some exemplary arrangements the handles may include other structures such as downward extending hook portions that enable the handles to engage with geo mesh grid or other structures that serve to vertically stabilize a testing sampler.

Figure 21:
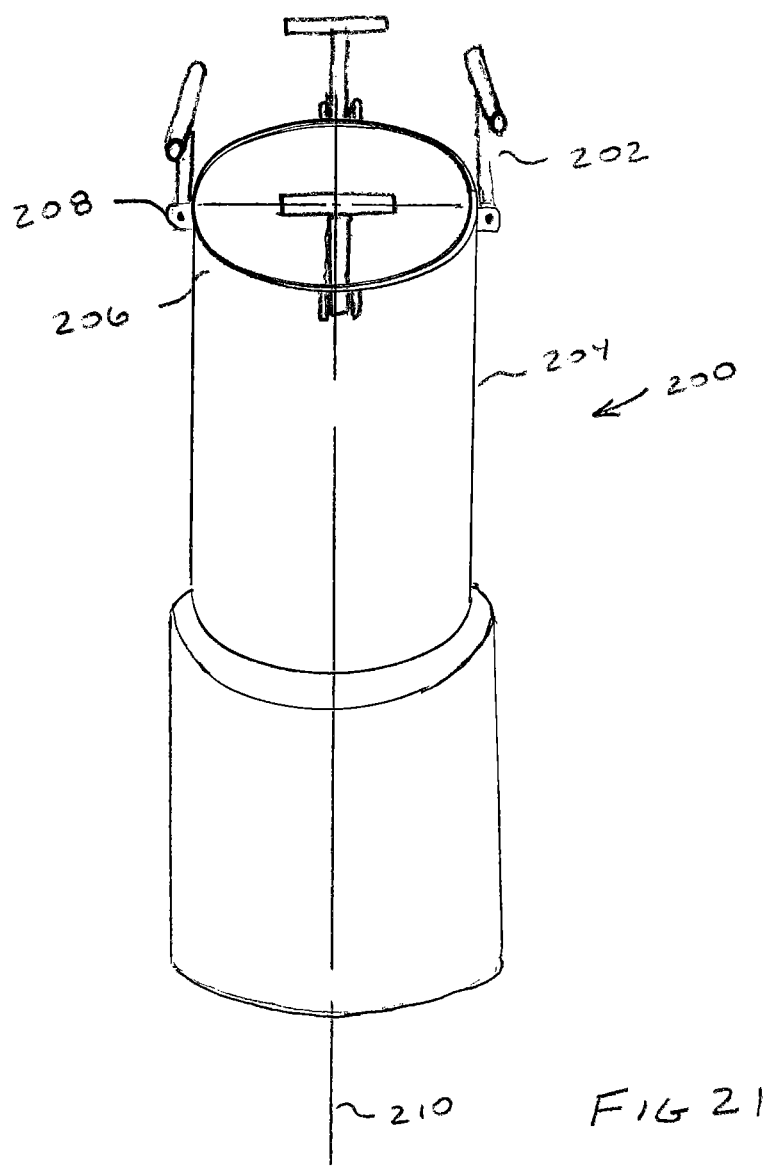

Once compaction of the concrete lift is completed, the exemplary handles may be moved away from the upper surface of the compacted lift to the position shown in FIG. 21. The handles are rotated about the pivots 208 such that the T-shaped handles extend vertically upwardly above the level of the compacted lift so that they can be engaged for purposes of extracting the sampler and the compacted sample held in the interior area thereof. In the exemplary arrangement the handles are moved to extend generally parallel to the axis 210. In some cases the handles are movable more than 90 degrees beyond the parallel position. This enables the handles to be engaged with a suitable lifting member or device so as to extract the testing sampler from the compacted lift. In some arrangements the handles are permanently connected to the upper area of the rigid tube, while in other arrangements the handles may be removable. Removal of the handles may be useful to reduce the size and weight of the tube transported to a laboratory for sample removal and analysis. Removable handles may be engaged to the tube using removable pins, fasteners or other structures.

Although in the exemplary arrangement four equally angularly spaced T-shaped handles are shown, other embodiments may use other numbers, configurations and handle shapes. For example some exemplary arrangements may include handle structures comprised of flexible loops, hooks, U-shaped handles or other suitable structures. In exemplary arrangements such structures are movable relative to the testing sampler and remain attached thereto during compaction and extraction. Some handle structures need to be moveable out of and above the surface of the compacted lift enough to engage the sampler for extraction. Exemplary arrangements may facilitate the taking of samples by reducing the time that would otherwise be required for attaching handles to the testing sampler prior to extraction. Also it should be understood that the exemplary handle structures may be utilized in connection with testing samplers which include only rigid tube portions or combination of rigid and deformable tubes and/or other structures. The handles shown and discussed our exemplary and in other embodiments other types of such structures may be utilized.

Thus the exemplary embodiments discussed achieve improved operation, eliminate difficulties encountered in the use of prior devices, systems and methods, and attain the useful results described herein.

In the foregoing description certain terms have been used for brevity, clarity and understanding. However, no unnecessary limitations are to be implied therefrom because such terms are used for descriptive purposes and are intended to be broadly construed. Moreover, the descriptions and illustrations herein are by way of examples and the inventive features are not limited to the exact features that are shown or described.

Further it should be understood that while the capabilities of the exemplary embodiments are described as being carried out by certain components and features, such capabilities may be accomplished using different components and features. Further the capabilities that are accomplished using a single described component may be carried out in other embodiments through the use of multiple components, and vice versa.

Having described the features, discoveries and principles of the exemplary embodiments, the manner in which they are constructed and operated, and the advantages and useful results attained; the new and useful structures, devices, elements, arrangements, parts, combinations, systems, equipment, operations, methods, processes and relationships are set forth in the appended claims.

I claim:

1. Apparatus comprising:
   an in-situ roller compacted concrete testing sampler including a vertically extending first tube,
   a vertically extending second tube,
      wherein the first tube and the second tube are in close-fitting concentric relatively vertically movable engagement,
   roller compactable concrete lift, wherein the concrete lift extends in horizontal surrounding relation of the first and second tubes, and wherein at least one of the first and second tubes contain a sample of such concrete lift,
   wherein vertical roller compaction of the concrete lift causes the first tube and the second tube to vertically relatively move and the sample to be compacted in like manner to the surrounding concrete lift.

2. The apparatus according to claim 1
   wherein one of the first tube and the second tube is comprised of deformable material and the other of the first tube and the second tube is comprised of relatively more rigid material,
   wherein vertical roller compaction causes deformation of the one tube due to relative vertical movement of the tubes.

3. The apparatus according to claim 2
   wherein the deformable tube is positioned vertically below the rigid tube.

4. The apparatus according to claim 3
   wherein downward movement of the rigid first tube is operative to cause a portion of the deformable second tube that extends within an interior area of the first tube, to separate from a remaining portion of the second tube.

5. The apparatus according to claim 3
   wherein the rigid tube includes an upper area,
   at least one handle, wherein the at least one handle is movably mounted in operative connection with the rigid tube in the upper area,
   wherein the at least one handle is movable to selectively extend either perpendicular or parallel to a central axis of the rigid tube,
   wherein the at least one handle is positionable perpendicular to the axis during roller compaction of the concrete lift.

6. The apparatus according to claim 5
   wherein the at least one handle includes a plurality of angularly spaced handles, wherein each of the plurality of handles operatively extends from an annular exterior surface of the rigid tube.

7. The apparatus according to claim 5
   wherein the at least one handle includes a plurality of angularly spaced T-shaped handles that are operatively connected to the rigid tube,
   wherein after roller compaction each of the plurality of handles is movable to extend parallel to the axis, whereby the rigid tube and the sample are removable from the compacted concrete lift by engagement with the handles.

8. The apparatus according to claim 5
   wherein an exterior annular surface of the rigid tube is coated with a nonstick coating.

9. The apparatus according to claim 8
   and further including at least one sample separator positioned horizontally within the sample, wherein the at least one sample separator is operative to separate the roller compacted concrete sample into vertically disposed sample portions, wherein a lower portion remains within the deformable tube when an upper portion is removed with the rigid tube.

10. The apparatus according to claim 5
    wherein an exterior annular surface of the rigid tube is coated with tetrafluoroethylene (TFE).

11. The apparatus according to claim 2
    wherein the deformable tube comprises a ring, and wherein the rigid tube comprises an annular pointed tip,
    wherein the tip is operative to deform and penetrate the ring responsive to relative vertical movement of the tubes.

12. The apparatus according to claim 2
    wherein the deformable tube comprises inner and outer concentric rings,
    wherein the rigid tube extends annularly and extends radially intermediate of the inner and outer rings of the deformable tube,
    wherein the rigid tube extends further vertically between the concentric rings with relative vertical movement of the first tube and at the second tube.

13. The apparatus according to claim 2
    wherein the deformable tube comprises inner and outer concentric rings,
    wherein the rigid tube extends annularly and extends radially intermediate of the inner and outer rings of the deformable tube,
    wherein the rigid tube extends further vertically between the concentric rings with relative vertical movement of the first tube and at the second tube,
    wherein the rigid tube is operative to radially deform at least one of the inner and outer rings with vertical movement therebetween.

14. The apparatus according to claim 2
wherein at least one of the first tube and the second tube includes an outer annular surface, wherein the outer annular surface includes a non-stick coating.

15. The apparatus according to claim 1
wherein the first tube is disposed vertically above the second tube,
wherein the first tube includes an upper portion,
at least one handle, wherein the at least one handle is in operative connection with the upper portion during vertical roller compaction,
wherein after roller compaction the at least one handle is engageable to extract the rigid tube with the sample therein from the compacted concrete lift.

16. The apparatus according to claim 15
wherein the at least one handle is in rotatable operative connection with the rigid tube,
wherein the at least one handle is movably positionable to extend either parallel to a central axis of the rigid tube or perpendicular to the central axis,
wherein the at least one handle is positionable perpendicular to the axis during roller compaction and is in contacting relation with an upper surface of the concrete lift,
wherein after roller compaction the at least one handle is rotatable to be generally above the surface of the compacted concrete lift and engageable to extract the rigid tube and sample therein from the compacted concrete lift.

17. A method comprising:
(a) embedding a roller compacted concrete testing sampler in surrounding loose roller compactable concrete lift, wherein the testing sampler includes a first tube and a second tube, wherein at least one of the tubes encloses a sample of the loose compactable concrete lift,
(b) subsequent to (a), compacting the loose roller compactable concrete lift such that the first tube and the second tube move relatively vertically to one another to compact the sample during simultaneous compaction of the surrounding roller compactable concrete lift,
(c) subsequent to (b), lifting the testing sampler out of the surrounding roller compacted concrete lift, whereby the compacted sample is available for testing.

18. The method according to claim 17
wherein one of the first tube and the second tube is comprised of relatively deformable material and the other of the first tube and the second tube is comprised of relatively rigid material,
wherein in (b) the tube comprised of deformable material deforms with relative vertical movement of the tubes.

19. The method according to claim 18
wherein in (a) the deformable tube is positioned vertically below the rigid tube.

20. The method according to claim 17
wherein in (a) and (b) the first and second tubes each extend about a central vertical axis,
wherein an upper one of the first and second tubes includes an upper area, wherein at least one handle is in movable operative connection with the upper area, wherein each handle is movably positionable to extend perpendicular and parallel to the axis,
and further comprising:
prior to (b) moving each handle to be perpendicular to the axis, wherein in (b) each handle extends perpendicular to the axis,
subsequent to (b) and prior to (c), moving each handle to extend parallel to the axis, wherein in (c) the testing sampler is lifted out of the compacted lift by each handle.

* * * * *